United States Patent
Matsuyama et al.

(10) Patent No.: US 6,258,935 B1
(45) Date of Patent: Jul. 10, 2001

(54) LSIRF POLYPEPTIDES

(75) Inventors: Toshifumi Matsuyama, Hirano-machi (JP); Alex Grossman; Christopher Donald Richardson, both of Toronto (CA)

(73) Assignee: Amgen Canada Inc., Toronto (CA)

( * ) Notice: Subject to any disclaimer, the term of this patent is extended or adjusted under 35 U.S.C. 154(b) by 0 days.

(21) Appl. No.: 09/195,940

(22) Filed: Nov. 19, 1998

Related U.S. Application Data

(60) Division of application No. 08/611,280, filed on Apr. 3, 1996, now Pat. No. 5,891,666, which is a continuation-in-part of application No. 08/422,733, filed on Apr. 14, 1995, now abandoned.

(51) Int. Cl.[7] .............................. C07K 14/00; C07K 5/00; C07K 14/52; C07H 21/04
(52) U.S. Cl. ........................ 530/350; 530/300; 530/351; 536/23.1
(58) Field of Search ................................ 530/300, 350, 530/351; 556/23.1

(56) References Cited

PUBLICATIONS

Berendsen, H. "A Glimpse of the Holy Grail?" Science vol. 282:642–643, Oct. 1998.*

Driggers et al, "An interferon γ–regulated protein that binds the interferon–inducible enhancer element of major histocompatibility complex class I genes", *Proc. Natl. Acad. Sci. USA*, 87: 3743–3747 (1990).

Eisenbeis et al, "Pip, a novel IRF family member, is a lymphoid–specific, PU.1–dependent transcriptional activator", *Genes & Development*, 9: 1377–1387 (1995).

Harada et al, "Structurally Similar but Functionally Distinct Factors, IRF–1 and IRF–2, Bind to the Same Regulatory Elements of IFN and IFN–Inducible Genes", *Cell*, 58: 729–739 (1989).

Sommer et al, "Minimal homology requirements for PCR primers", *Nucleic Acids Research*, 17: 6749 (1989).

Miyamoto et al, "Regulated Expression of a Gene Encoding a Nuclear Factor, IRF–1, That Specifically Binds to IFN–βGene Regulatory Elements", *Cell*, 54: 903–913 (1988).

Veals et al, "Subunit of an Alpha–Interferon–Responsive Transcription Factor Is Related to Interferon Regulatory Factor and Myb Families of DNA–Binding Proteins", *Molecular and Cellular Biology*, 12: 3315–3324 (1992).

* cited by examiner

*Primary Examiner*—Robert A. Schwartzman
*Assistant Examiner*—Sean McGarry
(74) *Attorney, Agent, or Firm*—Nancy A. Oleski; Steven M. Odre

(57) ABSTRACT

Disclosed are nucleotide sequences encoding a novel polypeptide termed LSIRF. Also disclosed are methods of preparing the polypeptide and uses thereof.

6 Claims, 33 Drawing Sheets

FIG.1A

| | | | | |
|---|---|---|---|---|
| ATGAACTTGG | AGACGGGCAG | CCGGGGCTCA | GAGTTCGGCA | TGAGCGCAGT | GAGCTGCGGC | 60 |
| AATGGGAAAC | TCCGACAGTG | GTTGATCGAC | CAGATCGACA | GCGGCAAGTA | CCCCGGGCTG | 120 |
| GTGTGGGAGA | ACGAGGAGAA | GAGCGTCTTC | CGCATCCCGT | GGAAACACGC | GGGCAAGCAG | 180 |
| GACTACAATC | GTGAGGAGGA | CGCTGCCCTC | TTCAAGGCTT | GGGCATTGTT | TAAAGGCAAG | 240 |
| TTCCGAGAAG | GGATCGACAA | GCCAGATCCT | CCTACTTGGA | AGACAAGATT | ACGATGTGCT | 300 |
| CTGAACAAGA | GCAATGACTT | TGAGGAATTG | GTCGAGAGGA | GCCAGCTGGA | TATCTCTGAC | 360 |
| CCATACAAGG | TGTACAGGAT | TGTTCCAGAG | GGAGCCAAAA | AAGGAGCAAA | GCAGCTCACT | 420 |
| TTGGATGACA | CACAGATGGC | CATGGGCCAC | CCCTACCCCA | TGACAGCACC | TTATGGCTCT | 480 |
| CTGCCAGCCC | AGCAGGTTCA | TAACTACATG | ATGCCACCCC | ATGACAGGAG | CTGGAGGGAT | 540 |
| TATGCCCCTG | ACCAGTCACA | CCCAGAAATC | CCATATCAAT | GTCCTGTGAC | GTTTGGCCCA | 600 |
| CGAGGCCACC | ACTGGCAAGG | CCCATCTTGT | GAAAATGGTT | GCCAGGTGAC | AGGAACCTTT | 660 |

FIG.1B

```
TATGCTTGTG CCCCACCTGA GTCCCAGGCT CCTGGAATCC CCATTGAGCC AAGCATAAGG   720
TCTGCTGAAG CCTTGGCGCT CTCAGACTGC CGGCTGCATA TCTGCCTGTA TTACCGGGAC   780
ATCCTCGTGA AAGAGCTGAC CACGACGAGC CCTGAAGGCT GCCGGATCTC CCACGGACAC   840
ACCTATGATG TTAGCAACCT GGACCAGGTC CTGTTTCCCT ACCCGGACGA CAATGGACAG   900
AGGAAGAACA TTGAGAAGTT GCTGAGCCAC CTGGAGAGGG GACTGGTCCT CTGGATGGCT   960
CCAGATGGGC TTTATGCCAA AAGACTCTGC CAGAGTAGGA TCTACTGGGA TGGGCCCCTG  1020
GCACTGTGCA GCGATCGGCC CAACAAGCTA GAAAGAGACC AGACTTGCAA GCTCTTTGAC  1080
ACACAGCAGT TTCTATCAGA GCTGCAAGTG TTTGCTCACC ATGGCCGGCC AGCACCGAGA  1140
TTCCAGGTGA CTCTGTGCTT TGGTGAGGAG TTTCCAGACC CTCAGAGACA GAGGAAGCTC  1200
ATCACAGCTC ATGTGGAACC TCTGCTAGCC AGACAACTGT ATTACTTTGC TCAACAAAAC  1260
ACTGGACATT TCCTGAGGGG CTACGAGTTA CCTGAACACG TTACCACTCC AGATTACCAC  1320
CGCTCCCCTCC GTCATTCTTC CATCCAAGAG TGA                              1353
```

FIG.2A

```
Met Asn Leu Glu Thr Gly Ser Arg Gly Ser Glu Phe Gly Met Ser Ala
 1               5                  10                  15
Val Ser Cys Gly Asn Gly Lys Leu Arg Gln Trp Leu Ile Asp Gln Ile
            20                  25                  30
Asp Ser Gly Lys Tyr Pro Gly Leu Val Trp Glu Asn Glu Glu Lys Ser
        35                  40                  45
Val Phe Arg Ile Pro Trp Lys His Ala Gly Lys Gln Asp Tyr Asn Arg
    50                  55                  60
Glu Asp Ala Ala Leu Phe Lys Ala Trp Ala Leu Phe Lys Gly Lys
65                  70                  75                  80
Phe Arg Glu Gly Ile Asp Lys Pro Asp Pro Thr Trp Lys Thr Arg
                85                  90                  95
Leu Arg Cys Ala Leu Asn Lys Ser Asn Asp Phe Glu Glu Leu Val Glu
                100                 105                 110
Arg Ser Gln Leu Asp Ile Ser Asp Pro Tyr Lys Val Tyr Arg Ile Val
            115                 120                 125
Pro Glu Gly Ala Lys Lys Gly Ala Lys Gln Leu Thr Leu Asp Asp Thr
        130                 135                 140
```

FIG.2A-1

```
Gln Met Ala Met Gly His Pro Tyr Pro Met Thr Ala Pro Tyr Gly Ser
145                 150                 155                 160

Leu Pro Ala Gln Gln Val His Asn Tyr Met Met Pro Pro His Asp Arg
                165                 170                 175

Ser Trp Arg Asp Tyr Ala Pro Asp Gln Ser His Pro Glu Ile Pro Tyr
            180                 185                 190

Gln Cys Pro Val Thr Phe Gly Pro Arg Gly His His Trp Gln Gly Pro
        195                 200                 205

Ser Cys Glu Asn Gly Cys Gln Val Thr Gly Thr Phe Tyr Ala Cys Ala
    210                 215                 220

Pro Pro Glu Ser Gln Ala Pro Gly Ile Pro Ile Glu Pro Ser Ile Arg
225                 230                 235                 240

Ser Ala Glu Ala Leu Ala Leu Ser Asp Cys Arg Leu His Ile Cys Leu
                245                 250                 255

Tyr Tyr Arg Asp Ile Leu Val Lys Glu Leu Thr Thr Thr Ser Pro Glu
            260                 265                 270

Gly Cys Arg Ile Ser His Gly His Thr Tyr Asp Val Ser Asn Leu Asp
        275                 280                 285
```

FIG.2B

```
Gln Val Leu Phe Pro Tyr Pro Asp Asp Asn Gly Gln Arg Lys Asn Ile
    290             295             300
Glu Lys Leu Leu Ser His Leu Glu Arg Gly Leu Val Leu Trp Met Ala
    305             310             315             320
Pro Asp Gly Leu Tyr Ala Lys Arg Leu Cys Gln Ser Arg Ile Tyr Trp
                325             330             335
Asp Gly Pro Leu Ala Leu Cys Ser Asp Arg Pro Asn Lys Leu Glu Arg
                340             345             350
Asp Gln Thr Cys Lys Leu Phe Asp Thr Gln Gln Phe Leu Ser Glu Leu
                355             360             365
Gln Val Phe Ala His His Gly Arg Pro Ala Pro Arg Phe Gln Val Thr
    370             375             380
Leu Cys Phe Gly Glu Phe Pro Asp Pro Gln Arg Gln Arg Lys Leu
    385             390             395             400
```

FIG.2B-1

```
Ile Thr Ala His Val Glu Pro Leu Leu Ala Arg Gln Leu Tyr Tyr Phe
                    405                             410                             415

Ala Gln Gln Asn Thr Gly His Phe Leu Arg Gly Tyr Glu Leu Pro Glu
                    420                             425                             430

His Val Thr Thr Pro Asp Tyr His Arg Ser Leu Arg His Ser Ser Ile
                    435                             440                             445

Gln Glu
450
```

FIG. 3A

```
AAGGGGCCAC CTGGCCATTC CTTCCTCTCC ACCAGCAACA ATGGGAGCAT GTGATTCACA    60
AGGGAATCAC ATTCAACTAA AAAGAGAAAC CGGGGTATGC TGTTTGCAAG GAACGGTTGA   120
AACTGGAACT CAATATGTCG TGTGGTGTGA AATAAACGTG TGTCTCACAT GTTTTCCCAT   180
GCTGGGGGCA GGGGTAAGAA AGTAAAAGGC AGACTGGTTA AAGACATGGG GTGGGGAGGG   240
CTGGAGGGAC GAGTGGTAAG AAATGGCGAC AGAGGAGATG AAGGTAATGT CATAATGAAA   300
CCCATCACTG CTGTGTGCAA CTAATAGATG CTAATAAAAT AGGAAGTTTT AATGATTAG    360
GTAGCTTATT GCTTGCATTC ACCTCACTGT TAAACTATCA CTTCTGGGGG ATCCACACAA   420
CGAGCGAGCG AGTAAACCAG AAGATGGCGT TGGAAGATTA GTAATCATAT CTTTTAAACA   480
AGATAACCAT GTGAAGTCTC AAAAGGTTTC TTGTAATGAC TGTTGTTTAA ACTTCTGAAA   540
ACAGAGGATG TAGATTGGCT GAGGAAAATG TTGAAACCGC CTAAGTCAAG GTAGAAGACA   600
CGTGTGTCTA AGTGAAAAAA AGAAAAAAGA AAAAAAAAAA AACCAAAAAC CTCGGGTTGG   660
CTGCTTCTGT CCTTAGTCTG TGCACGCTTT GAAGAAATGT AATTCCTCAG CAGCAAGGCT   720
GTGCTATCTG AAGCTACAAT CTCTGCTTTG CTCCGAGGTG TGTCTCTGGT GACCGGGATA   780
GTTCCCGACA GACAGAAGGT GTTCAAAGAA TATTTTTGAA TGAATGAAAC CCCAAAGGAA   840
```

FIG.3A-1

```
GAAGAGGGGA AAATGGGTGT GACCAAAATT TTCTTTGAAC GAAACTCTGT TGTTTACTAC    900
CAGGGCTCTG ACAATGGAAA ACTAATTGGG GTGAAAGAAC GACATGGCAT CCTGTTAATT    960
TCTGAGAAAG CCTGTTGATG TTAGGAAAAA AAAACATGCC GGTGGGCATC TCTGCACCAG   1020
TTTTCCTGTG GCCAAAATCA GATGTTTCTC CTAAAGTCCA GAACCCAGGA TGGAAGATTA   1080
AAAGAAAAAC TGAGAAACAT GTGAAATGAA AAAGTTGTCA AAAGCTTTAC AAACGCTCCA   1140
AGTTGACCTG TGGTGGTGGT AATCTAAAAT GATACAGAAA CTGGTAGTCT GCTTGCTTAC   1200
CTGAAAACAC CAAGATAACA TATAAGCTCC AGGCATCCAA GCTGAGCTGG AGAAAGTCAG   1260
CGGCAAAAGC TCATGGAGTT TACATATGAA GGTCAAAGAA AACACGAAAA TAAAGTAAAA   1320
CCTTCAGTCA GCCTAGCTGT TCTATTTGGG GCATTGGTAC CTCACCGCCA ACTGCCTCCC   1380
ACGAGGCTGA GGTTAAAATT ATCATTTTAA GGTGAATTGA CATCCGGAAG CGCGCTAACT   1440
ACCTGAGTAC TCAGGGATCC CCCATCTCTT TTATGTTGCC ATGATTGAAA CTTTGGGGAC   1500
TGTGCTTGTC TGAGTCATCT CAATTCGTCG GTTTCATTCA CCCAACATGT ATAAGCGTTT   1560
CAAACACAGT ATTTGGGCCA CGGCTTATAA ACTTGCCTTT CTATTTTTCT TTTTAGTGAG   1620
CGTGATATTC TCTAAACGCT CAGAGAGACA AGACTCCGCT TTGTTCAGGA TGCTCCCGAC   1680
```

FIG.3B

```
CTCTCTCAGT CTATCTCTTC TGTTACATCT GTGAGAACAA GTTCCCTGTG CTCCAGACTC    1740
TCCATCACTT CCCACCTGTC GATGAGCAGT TAGTAGTTAT CAGCTATGCT CAGTGCAGAT    1800
TCCAGTATCC CCTTTGTATG CCTCCACCTT CCACAGGAGG GGGGCCATAC CGACTTGTCC    1860
CATCCGGTTG AGGATTTCTG AGTACATCAG AGTCCCCAGC CCCCTCCACA GGAGGAGCTG    1920
AAGAAAGCCA GGGTTTGTCT GAAGTGGGAC AGCCCTTGAC CCGGTGGGCT CTAGTCCGAA    1980
GCTCCTGTTC CTGCGGGACA CCCAGGCACA AGGCAGAGGT GGGGGGCGGT CCTGGGTATG    2040
GCCAACCCAC GCCCTCTCAA GGCGGGGCCG AAGCGCCCGC CCTGCACTCC GCCTCCGGCT    2100
CTATAAAGTT CCTCTTTCTC ACCTCACTTT CCTAGTTTC                           2139
```

FIG. 4A

| | | | | |
|---|---|---|---|---|
| ACCACTTGAA | CTTGGGACCC | TTTGCTGCCC | TCAGCTAAGA | GTGCGGGTGA | GGTAAGGCCT | 60 |
| GTAGTCGGGC | AGAAGGAGA | GTGTGAGGCT | GGTGGCAGAG | GAAGCCTGGC | TTCCATCTCT | 120 |
| GAGCCTGAGG | GAGAATGCTG | AGATAGCGGA | CCCAGGCTCC | GCTCATCTAC | GCTGCCCTAG | 180 |
| GACCTGTGCA | CTTCGGGTTT | TGTATGAAGC | TGTTTGGGTG | GGAGTTCCAG | AACATCCCCC | 240 |
| ACGGGCTGGG | CGGGACGAGC | TAATGGGACT | GTGGTGTCAT | CAAAGGATCG | CACTGGCCAC | 300 |
| AGCTTGTCCT | CAGAGGGACA | GCCTCTGACT | CTCTCTGCTC | CAGTGGAAAG | CTCCTTTCCA | 360 |
| GCCCTGGTTC | CTAAAGGACC | CAAACTCATC | TAGGGCTCCA | GAGCGTGATT | CCTAGGCCGG | 420 |
| GCAGCCAAGA | AGAGCTGAGA | GCTCCAAACT | TAGGGTGCTC | AGAGCCCCTT | TCCCCGCATG | 480 |
| CCCCTTCTTC | ACTTCTCTGG | CAAGAGTGCT | AGTGTTGCTG | TCCGCAGCAC | CCCTTATTCC | 540 |
| CAGCCTCGGC | TTCATTCCTG | CCAGGGTTCG | CGCTGACATT | CTGCAGGTTG | GAATCTCCTG | 600 |
| TTTCTTGGCT | GCGCTGCTTG | CCCCATAACC | AGACTTCCAC | TTGTTGCTTC | CAGGACCCAC | 660 |
| GTGATGGTCT | CTGGTTGGGT | AGGCCTGGGG | TTATTCCGAG | GACAAAGTAA | GGGTGTCATA | 720 |
| GAAGAAAGTC | AAGAGAGTAA | GCTAGGTMCC | CCAAACCTGC | ATGGCAGGGA | CACAGGACCT | 780 |
| GGACAAGGGC | TAGTCCATGT | GCCAGGTCCT | TTTCGCCTGG | GGCAGCCAGG | GCAACCTAAA | 840 |

FIG.4A-1

```
CCCAGGAAGG GGCAAGTGTA GAAACAGTGA GGGAAAAGTG GGATGAAAGC TACTTGGATC    900
CAGCACAGAG GGACGAGTGA CCAAAGTGAG CGCCCCAGCG TGGCGCAAGA CTTGGGATCT    960
GCAGAGAAGC TGTGTAGCTA GGAGCTTTCA ACGGAGCGTG TTAATGTAAA TGTAAATGAA   1020
GAAATTACCT AATTTTTTA ATAAAAGAAA GAACAGACAG GCAAAAAAAA AAAAAGGAGG   1080
AGGAGGAGGA GGAGGATGGT GCGCGCCAAG GGATGCTCTC TATACCTTCG TCAAAGTACC   1140
TTCTCTTGGG GGACTTCGGA GACTCTGTCA CTGCACCCGA GCACCTTGTC AGCCTCAGAG   1200
ACTCGGGGCC TCGTGGGCAC TCCAAGAGTT TGGGACGGGG CTTCCTCCCG CCTCCAAAGT   1260
GATACGAAGG TAGTTGCAGG GAATGTGTGT CTCTCCTCAG CGCACAAGCC CAGGAGGAGG   1320
TCCCCACGCG TCATGAACTT GGAGACGGGC AGCCGGGGCT CAGAGTTCGG CATGAGCGCA   1380
GTGAGCTGCG GCAATGGGAA ACTCCGACAG TGGTTGATCG ACCAGATCGA CAGCGGCAAG   1440
TACCCCGGGC TGGTGTGGGA GAACGAGGAG AAGAGCGTCT TCCGCATCCC GTGGAAACAC   1500
GCGGGCAAGC AGGACTACAA TCGTGAGGAG GACGCTGCCC TCTTCAAGGT TAGCAGCATT   1560
CAGGGATCCC TGGGCAGGGG GATGGGAATC CTGAAAGCTC TGAATGTCTG    1620
TGGCTCCCGG GCAAGGGACT AAGAGGTGGG CTCCTGCAAG GAGGAGGCCA GAGCATCAAG   1680
```

FIG.4B

| | | | | | |
|---|---|---|---|---|---|
| CATTGGACCC | TGCTTAGGCA | AAGTCCCCAG | GAGAAGGGAA | AGAGGTTGCA | AACTCTCCGG | 1740 |
| GGATTGCATA | CACAAGAAAC | CAGGTCCCAA | TACTGTTTGT | GTGGAGGAAA | GAACTTCCAG | 1800 |
| CTTCAGGGGC | ATCTCTGGGG | GACCGAGGTT | CCGTTTGCAT | AGCCCATTCG | CTGTTTCCTG | 1860 |
| CCACCACCAC | CGACTGCTAG | GGCCACTCTC | TGCTTCCCTG | TCTCTCTGTG | TTTTGTTATT | 1920 |
| TTTCTGAGTT | TCTCTCTCTG | GGTTTTGTTT | CTTTGATTGG | GCACCTCTAC | TGTCTGGTTC | 1980 |
| TAGTTCTAGA | AGCTGCGATC | TCTGATTTTC | TTTCTTTGAG | TAGCTTTGAC | TATTCCGAGT | 2040 |
| CTTTCTCTGG | TATCCCCCTC | CGACCCCGTG | TGAGTCCCTT | AGGACTGATG | TCCCCAGAGA | 2100 |
| ACTGGCTCAC | TGAACTGTGA | AGCCCCCAGC | CTCCACCTGC | CAGCAGGCCG | AGGAAGGGGA | 2160 |
| CTTCCTGCGG | GAATTTGTTC | AAAGTACCTC | TGTGATTTTG | TAGATGTCCT | CTCTGGGGCC | 2220 |
| TGCCCCCTCC | ACAGCTCTGT | CCCCAGTCTT | GCCCACACTT | GATTCAGGCG | CTGGGCGTGT | 2280 |
| ACAGCCCATA | CTAGGGGTCT | CAGGACCCCA | CTAACATCAT | GTTCCACATT | TCAGGCAACA | 2340 |
| GCAAATTTGA | AACAGTAACC | TTCCTTGCTG | AAATGCAATC | CATAGAATTC | TTTTGACGCT | 2400 |
| CTGGGCTTGA | CTTTTCTTAT | CATCGTTCTT | AGGCTTGGGC | ATTGTTAAAA | GGCAAGTTCC | 2460 |
| GAGAAGGGAT | CGACAAGCCA | GATCCTCCTA | CTTGGAAGAC | AAGATTACGA | TGTGCTCTGA | 2520 |

FIG.4B -1

```
ACAAGAGCAA TGACTTTGAG AGAGGAGCCA GCTGGATATC TCTGACCCAT    2580
ACAAGGTGTA CAGGATTGTT CCAAAAAAGG TAAGGGGTTT TCCCAGCCCA    2640
GGTGGCAGGA TAAAGGCATT ATGGCACTCA GAGAGCCCTT CTTCCTAGAG ACAGTCACGT    2700
CCTACCTCTG CTGTAGGTTA AGCCCAGATG TCCTTTTGCC CATGTCCTCT CTGTTATAAG    2760
TGACAACCCT GTGGTGTTAG CCTGGCAGAC TTTAAGCCCC CAGTTAGGAT ATGGGTGTGT    2820
GGGTTATGCA CTTGAAGGCA TTATTTTCAG TTACTCCATT CAGTTAGGAT CTGGATCAAA    2880
TTTCCAAACA AAATCTGGAA ATGTTTACTT ACCTAATATC CTCTAGTAAG    2940
CATTTTCAAG AGGAGAAAGC ACATCCCACA CCCCATACAT ATTCACACTT CTTGTAATAA    3000
AACTGCTAGA GTTTCTGGTT TAACATGGCC TGCTAGGGTG GTTATGAATA TTCAGATCTT    3060
GAGTTCCCTC TCTTCCAACT AGTCTACCTC AAGCAGTGCT CAGGAATCTG CATTGGTTC    3120
CAACCATACA GGATGCCTTA ACTAGGTACC ATCTCACAAC CAGAAACCAC TTGGTGGATC    3180
ACAGGGATCC TGGGTGGTGT TTCCTTCCCT GGCTGTCACT CACAAGTCAG CAAATGTTTA    3240
ATCAGTTTAA TGGCAAAGAC AAATATCTCT CTAAGAAATT GCTTGAAAAA CAAACAAACA    3300
AACAAAAACAA AACAAACCTA AAATACCCGA TTGGTTAATA GGGCTATGCA TTCTAAGAAT    3360
```

FIG.4C

| | | | | | |
|---|---|---|---|---|---|
| TAAGTGCATA | GGTACTTTTA | TAAGATTTAA | GTCAGTTCCT | TGTCTTACTC | TGTGTTCTCT | 3420
| CTTCCTTTTC | CCCAAACACA | CAGGAGCAAA | GCAGCTCACT | TTGGATGACA | CACAGATGGC | 3480
| CATGGGCCAC | CCCTACCCCA | TGACAGCACC | CTGCCAGCCC | AGGTATGTGG | 3540
| TAGACTCTTG | GTCTTGTGGA | AGGCTGGCCC | ATGCCCTTTT | GACTGGCTCC | ACACAGAGAG | 3600
| GCAAACACAA | ATGAAAAGTG | TAGGGCTGAC | TTCTTATTTG | CTATGGCTAG | TACACACGCT | 3660
| GAACAAAAAC | TTGGTCAGAG | AAGGATGTTT | CAGTTCCAGT | GTGGTGTCAC | TGTCCCTGAC | 3720
| GCCACAGTTT | TGTTGGGGAG | TTTGATGTGT | CCCACCTGTG | GAGAGAGGCT | TCCACTGATG | 3780
| GTCAGATCTT | CTGGGAATCA | GACCTTTTGT | GGAAGTCAAA | GGTTTTGGAA | GTAGTACTTT | 3840
| ATCATGTGAA | ACCGCAGAGC | AGCTGACTTC | TCTAGGCGTC | CCTGATGTGA | ATTACAGTAC | 3900
| TGTTTTATTC | ACTTTGGTGG | CTTAAAAAGG | GCAGATTTCA | CTGCGGTATT | CTTGGTGCCG | 3960
| TGTTCAGCCA | TATGATGAAG | CCTTACAAAA | ATCACAGCTT | TATACAATGT | CCTCATTGTG | 4020
| CTTTCAGACC | CTCTATGGCT | GTTTTTTACC | TAGTGTGATA | GACAGTCCAT | GTCACTTTTT | 4080
| GGGCAAAATG | ACTTGGCTGC | TGGACAAAAA | AAGGGGTTCC | CTGAGGAGTT | TGGGTGATAT | 4140

FIG.4C-1

```
GAAAGGACTC CGACACCCMC TGATGTCTTC CTCTTAGCAA TCCCTGTTCT CTGTCAGCAG  4200
GTTCATAACT ACATGATGCC ACCCCATGAC AGGAGCTGGA GGGATTATGC CCCTGACCAG  4260
TCACACCCAG AAATCCCATA TCAATGTCCT GTGACGTTTG GCCCACGAGG CCACCACTGG  4320
CAAGGCCCAT CTTGTGAAAA TGGTAAGGAT TGTGCCAGGG CAGCAGACAG AAGAACAACC  4380
TGAGCTCGGG GTGTGGACAG CACCACAGGG CTTTTCCCTA CCATTGAGAT ACCAGAGACA  4440
CATCATATGA AGCTGCTACT GTTGTTGTTG TTGTTGTTGC TGCTGCTGCT GCTGGGGTGG  4500
TGGGGTGGTG GGKTGGTGGG GTGGTGGAGT GGTGGTGGTG GTGGGTGGTTG TGGGGTGTTG  4560
GGGTATGTTG CCTTGTCCTG TGAAATGTTG AAGTCCTTAG ATCCATGATA GGCCCTCAGTC  4620
TGTGTGGGGA CTTAACTAGA AGACCCCAGA GATCATTCCA AGTAGCTGAA AAGTGCCCCA  4680
TTTTTAATAC ATAGAGAAAA ACATGGATGA CAACAAATTC TCAATGACAA GTAATGTCAA  4740
TTATAAAACT CGTCTATATT TTGTTTTAAC TTGAGTTATC CCTTATTTCC GATGGTGATT  4800
AAGTTGGGGG GTTTGTTGTA TCCCACCTAT CTCCCTAGTC TGTATCTTTC TACTCTCCTG  4860
TAAAGTAGAG AGTTGTACCC AGTCCACCTC AGCAGGAAAT CATTGCTAGT TCATGTCTCT  4920
TGAATAATAA TGAGTCATCT ATAGCTGTTC TTGGTACTAA GGAAGGAAGG ATCAGAGCGA  4980
AAGTAATCCA CAAAGTGTCT CTACAAATGA GTGCCCTGCC CGAAAAGACC CACAGGGGTC  5040
```

FIG.4D

```
CCCCCATGCT AGCTGGGCTC TCACAGAAGA AACGCCCACT AACCAGACAC AAAAAAATTT    5100
CACAAACTAT GTTCAGTGAG ACTTGGGTCC TTTAGTGTTT ATTTAGGTGA GTGCACCAAG    5160
CTCCACCTCG GGTCCTTTTT TGGCTGTGTA TTTTAAGGTA GAGTCTTGCT AAATTACCAA    5220
GGCTAGGATC TTCCTGCCTT CAACTCTTGA GTAGCTGGGA CTACAATCTT GTTCTARCGG    5280
GCTGAACATA AAACAAGTTT TTAGGACTTR CAAGTTCACT GTTTAAATAT AAGTCTTGAC    5340
ATGGGTCGCC GTGCGAGTAG TTCTTTTATA TTGTTCTGGC AATACTTTAC CTTGTGACAA    5400
TTTCATCAAC ACCCTCACTC AGTCTGTGCA TGCTTACACT AATCTTGCTT TAGTGTGACA    5460
TAACTTCTCT GCTGCCAGAG AACACGGTTC AGCCCCTCCC CCTAGCTAAC AAACAGTGAG    5520
CAGAATAAAT GAGGGTTGAA TAATTAATTC ATCTTTGAAC TAGTCTTATA GAAGTTTGAA    5580
CTCTGACCCT GCTGGTAACT TGCTATGTGG GCTGGGTGCAA GTCCCTCTCC TTCTGGGCCT    5640
CAGTTTCCCT ATAGATTTGG AGTGAGCCCC AGGTTTCCAT CCAGAGCTGT ACTGTGGCTC    5700
CTTCCTTCAT CACCCTAATT TTTATCACTG GATGTGGACT TTGGACTTTG TCCCATAATC    5760
ACACGTTATT CTGCTAGCAG GTGCTTAGAG GCTGTCAGGC TTGGGTTGGA GGCCATGGCC    5820
TCTCCCAACT CAAGAGCCTC CCCGCACTCA GACTCGATAC TTAGACATCA TCTGATTTTT    5880
```

FIG.4D -1

```
ATTTKCAAAT GCAGGTTGCC AGGTGACAGG AACCTTTTAT GCTTGTGCCC CACCTGAGTC    5940
CCAGGCTCCT GGAATCCCCA TTGAGCCAAG CATAAGGTCT GCTGAAGCCT TAGCGCTCTC    6000
AGGTGAGTGT GGCGCTTCCT GTAAAGCTCC GAGGGAGGGG GCATCTCTCC TCTACTGAGG    6060
TTGGGTGAGG ATTAGACTC TCGCCTTGCA GGCCCCGGGG TCTGGAGTAG GCATGGTCCA     6120
GGCTATGTGG ACATCACGCT GAGTCAAATA CACTATTAGA AATCTCCACA GCAGTACCAG    6180
CTAGCCAAAT ACTATTGGA CGATGTCTTT AACCTTCTAC ATCATTACCT GCCCAGTTTT     6240
CCAAGGAATGT GTAACCAGGC TCCTCCTCCA GCCGACATTC TCCATTCTCG CAGTGTGGAA   6300
AGGCTTTATA GGCACAAAAG AATGCTGTTT GTCCTTTTAG GGTGTAGGGT TGGCCACAAA    6360
CAGGTGGTCT GAGTTGCTTC CAAGGAACAC TGGTTCTGAA CCCTGGGTCTC TGAGAAGTTC   6420
TTATSCCCCC TAAAGGATCA TATAGGTCTG ACTCCCTCAC AACTTTGACA GAATTGCTGA    6480
GCATGTGTGG ATGTGATCTG ATTTTAAAGT TCTGTTACTA AGGAAGCCTG CACTGGAGA     6540
TACTGACCAG CATTTTAAAA GCCCACACTC CGTGGAAGCA GACATCTTAT GTCCATTTAG    6600
TCTTTAGATG ATTTTTTTGG ATGTTTTCAA ATGGAATTAT TAGAATTCTC ATCATGCCCT    6660
CGGCTACCTT AAAAGCCTCT GACTGAAAAC ATCAACTGCA ATCAACTGCA TTTGACAAT    TTTAGACACT    6720
```

FIG.4E

```
TCCCTTGTTC TCGAGGGAGG AAGAAGTTTT AAAATCTAGT TCCTTCCAGC TCTGATGCTC    6780
AGGGAGACTT TGTGAGCCAC TCAAGAACAG CCGAGGAGCA CATCTGGGCA TCAGGGGTTG    6840
TCACAGACAC TAGAATGCTC TAGATCCTCT TCTGGAGCGC CAAAGACTTG TGTGGGTGCC    6900
CCAAGAGTAG GAAATAAACA GCTATTTATA TCTCTGCAAT CTTGTGATTT TGGTGACATT    6960
AAATGAAATG AAACCTGCCC TACCACTCAC CTCAGATGGC CAACGCCCCC TCTCTTTGGG    7020
TGCACCACTT GTGCTGTTCA TAGCTGCAGC TATCGAAGAC ACCATGATGT GGGCTGTCAG    7080
AACTTGCCAT TGAAGAATAC GAGGCTTTTG TGGGTTTCTT CTTCTAGTTT GCATAATTAA    7140
TTATCAACCC TGAGTGCACT TTTCAGAAAG CTATTCTTTC CAGGCATTGT TGGGGCTCCA    7200
ACCACCAGCA CGGGTATCTA TCTCTGCCTG GGGAGCCCTT TGCACACCCA GCTTGCCCTT    7260
TCGGCCCGTG GGTGGTATTT TAAAGTGGCT TCTGAAATCA ACAAAATCAT GTGTCAATAA    7320
ATTCCTGTCT TAAAGCTGTA GAAAACCTAG TTGTTGGGTT CTTTTCAGAG TTGAACACGA    7380
AGCTTAGAGG GATTTCAGGG GGTTTTACAT TAMCCACTGG CTTTTAGAGC AGCTCTCATC    7440
AATTTCTTCC CCTACTCCAA GAGAGCTGAC TTAAAAATAA GAAAATAAAG GTATCATTTT    7500
CCAGAGCCCA GAAATTGTTA TTTTAGTGCC TGTCTCTAAC ATATCTATGT GGGTTTTGTT    7560
```

FIG.4E-1

```
GTTGTGTGGT TTTACTTAAT GACATCATGG TAACACCTTA GGGAAGTTCC AGAGCTGAGG 7620
ACACTATTTG CTTTTCTTCT AAGATGTTTC TGTATTTCTT TTACTAATAG AAATCTGTCC 7680
CAGAGGTCAA CTCCAAAATC AAAATTGAGT TGCTGGAAAA CGAATTCCAA TTCGGTAGTA 7740
TTATTTCATA TTGTAGACAA AATGCCACCA CTGTTAACAC CATCATCCGA AAAGCCCTCA 7800
TAACAGGGGT GTGCTTTCTA ATAAAATTTG GCTGAAAATT CAAGAAATAT ATACCTCTCC 7860
CCAAGAGAAG TAAATGGCCA CAACAACATT TGAAAAATGAT CGTGTTAGAG AGATCAGTTT 7920
CTTTCCACAA GCTTCTCTTA GTATTCGTGT CTTGAGGTCT AAGAATCTAC AGGGAATAAG 7980
AGCAGCTAAC ATCTCCAAGA CTTCCTTGGT CCTAGGATCT TTCACTTGTT CGTGGAGCAT 8040
CTTGACACTC AAGTGTTCCA CCTGCTGTCC TTCGTATCAG TCTAGTCACC GAGTTTTTGG 8100
GGCTCTGAGC AAGGTGGCAC CTTTTTCAAA TCCATCAGCA CTGACTCCAG AGTTTTGTTC 8160
ACAGACTGCC GGCTGCATAT CTGCCTGTAT TACCGGGACA TCCTCGTGAA AGAGCTGACC 8220
ACGACGAGCC CTGAAGGCTG CCGGATCTCC CACGGACACA CCTATGATGT TAGCAACCTG 8280
GACCAGGTCC TGTTTCCCTA CCCGGACGAC AATGGACAGA GGAAGAACAT TGAGAAGTTG 8340
CTGAGCCACC TGGAGAGGGG ACTGGTCCTC TGGATGGCTC CAGATGGGCT TTATGCCAAA 8400
```

FIG.4F

```
AGACTCTGCC AGAGTAGGAT CTACTGGGAT GGGCCCCTGG CACTGTGCAG CGATCGGCCC   8460
AACAAGCTAG AAAGAGACCA GACTTGCAAG CTCTTTGACA CACAGCAGTT TCTATCAGGT   8520
AACACACCTC ACAGTCTGTT AGAATGGAGG TGGTGGTGGG TGCTGGCTAT AAAGGTCTCA   8580
AATGGCAGTG TCTGCCTACC CCAGACAGAG GTCTTCCTCC TGAGATCTGT GAGCTCATGC   8640
AGAAATAGAA TTCCTGCCTG ATTCATGCCT AGCCTTTGTC TGTTGTGTAC TCCCCTGATT   8700
AGCAGAGGGC CAGAAAGAGG ATCCATATTT GCTGCCCAGG ATAGACACTG GTGTGGGTTG   8760
ATCTCTTAAT TTATCATCAT TCTTTTCACT CTAGGCTTTT GTTTGTTTG TTTTGTCAGA    8820
ATATATGTAG CTCAGGCTGG CCTAGAACTC CTGCCTCGGG ATTTTATCTG TACACCAGCA   8880
CATCTGGCCA ATGAATTAAA ATGTGGGCTT TCAGCGGCAT GTGCCCCACC CCCAGAGAGG   8940
TTTCACTGTG TTGGCTCTCT GCTCTCAGCA AGTTTATCTG CTGACACCTC AGCTCTTTAG   9000
GGGTTTCTAG AAGCAGTTCG GTTGCAGAGA GCAGTGGAAA TCTTTGATGT CTACCCATTC   9060
TGGATTTGCA CCCCACTAGG GACAGTCCCC ATAGGCACAG TTGAGAATTC ATATCTGATC   9120
AGGGCAGAGT CTTCATGCCT GCTCTGTGGA GGCAGCTTTT TAATGTCAGT TCTTTGATGC   9180
AGACAAGACC TGGGAACCTA GCTCTGGGAG GAGGAATAAA GGTTAATGCC AGTGAGTGGA   9240
```

FIG.4F-1

| | | | | |
|---|---|---|---|---|
| TGTGGCTTTC | TGCTTGTGCT | GGGGGAGGAA | GCCAAGGCCT | TGCACATACA | AGGCAAGTGC | 9300 |
| TCTGCTCCAA | GTGGCGATGC | CCCCAGCCAT | GGGCAGGTTT | CTTTTCAGCA | ATCTTGTCTG | 9360 |
| TTTCATGTCT | CTCAGGCAGG | ACTAGCCTCA | GCATGACATC | CTTGTCAGAG | GGGCTTCATT | 9420 |
| GGTCCCCTTC | TCCCTGTATC | CAAAGTGAGA | TTGAAGCCTA | CTCTGGTTCT | | 9480 |
| CCAGTTATGG | AGTTTTAGAC | CTAGTGCCAA | GTAGGACACA | GCTGCCAACA | GCTGGTGAGA | 9540 |
| GAAACAGATG | CTCTTGGTGC | CCAGACACCA | CGTGGCCTCC | ATGGTTAGCT | AGTGAGGTTA | 9600 |
| AAAAAATAAC | CCTGGGCCAT | CAGAACATTG | TGACTCTTTA | CATTAAAATG | TCTCCTTGGC | 9660 |
| CTGTGCTGAT | TGCTTGACTC | AGCATGGCTA | CTTTTCTTTT | TCTTCTTTGT | CTTCTTCTCT | 9720 |
| TTGACCTTGT | GCATTTCTGT | GAGTGTAGTG | CTGCAGACCC | AAGTTCTTAA | GGTTGGGTCA | 9780 |
| TGTTCCTTAA | GAGTAATGAA | GTAAAACCAG | TKCCAAGTCA | GGAGATCATA | TGTGAACTTG | 9840 |
| ACCATGTGAT | TTTGTGTCTA | GGGTCTGCTC | TAAGGGCTGG | ACTTAGGGGA | ACAGAGCCCG | 9900 |
| GGCTCTCCCA | AAGCAGACTT | CCACGTGACT | CTGGCTTTCC | GTTCACCCGC | TTTACCAGGT | 9960 |
| GTCTGAACAG | TTTGGTTTTT | TTTTTTTCTTT | CTTTCTTGTG | GGTTTTCAGA | GCTGCAAGTG | 10020 |
| TTTGCTCACC | ATGGCCGGCC | AGCACCGAGA | TTCCAGGTGA | CTCTGTGCTT | TGGTGAGGAG | 10080 |

FIG.4G

| | | | | |
|---|---|---|---|---|
| TTTCCAGACC | CTCAGAGACA | GAGGAAGCTC | ATCACAGCTC | ATGTGAGTAC | CTGGTTACAT | 10140 |
| CACCCGTAAA | TCACACACTG | TGGAGCTGTC | CCTTTTAGAG | AAGTGGCAAG | TGACGAGTAA | 10200 |
| ATGTCAGCTC | ACCTGGGAAA | ATAGATGTAG | ACCTTAAAAT | AGTGCAGGAG | GAAGCAGGCT | 10260 |
| CCAGTGAACA | CCACAGCTCA | GGGAGGCACC | CGCAACCTAC | TTCCAGACAA | ATTCTGTCAC | 10320 |
| CACCGAATCA | GCAGGGCAGA | TGACTTGGAC | CCAAGMTCT | GTTTGTTCTG | TATTCTTTAT | 10380 |
| TGTTTCATAC | AGACAGTTAC | CTGCCCTTTT | ATAGGAATTT | TCAATAGTTG | GGACCAAGTA | 10440 |
| CTGCCCTTCG | ACATCTCTGT | TTCTTGTGTG | GTTTTAAAGA | TGCTGTCCTT | TCGAGTAGAG | 10500 |
| TAGCACTTTC | TCCCTGGGAG | GCTGCCTGTT | ATGTATTATG | CTTCATCGGG | CCTCCTAACT | 10560 |
| TCARATAGTT | CCCAGACCCT | CGCTTTGTTG | CTGGACTTTA | GGGAGTTATT | TAACAGTTGG | 10620 |
| ACAAGGGAGG | TGGAGGAGGC | TGAGTCTTCC | CAGGAATCAG | GTAGGTCGGT | CTATCCTCAC | 10680 |
| AGCTAGGGTT | TATTCGGATA | ATGTTCATCA | CTCACTTAAT | AATTAAAAGG | TAATTCTGAA | 10740 |
| TACATGATGT | TTTTTAATTA | GAAAATTTTA | CTTAATTACA | TATCTTGAAA | AGTATGCAGT | 10800 |
| GTGGAGTAAA | GGTTGTGTCC | CAGATAGCCA | CAATATCTCA | GTGCAAATGG | GATATTAGCT | 10860 |

FIG.4G-1

| | | | | |
|---|---|---|---|---|
| CTGATGATAT | CTCTTAGTGG | AGACTGAAGA | CTAGGCATAC | AGCGCAATGG | AAGGCATTTG | 10920 |
| CTAGGCAGTG | GTAAAGCCCT | GGGTTCTAAA | CCCCGCCTAG | GATGGGGGTT | GGGCACTGAT | 10980 |
| GTTGAACATC | CAGCCTCCCT | TCTCGGTTGG | AAAAAGTAAA | ATCTAAGAAG | CAACAAACGG | 11040 |
| GCTGGAGAGA | TGGCTCAGTT | GTTAAGAGCA | CAGGCTGTTC | TTCCAGAGGT | CCTGAGTTTA | 11100 |
| ATTCCTAGAA | ACCACATGTG | CCTTACAACC | ATCTGCAGTG | AGCTCTAATG | CCATCTTCTG | 11160 |
| GTGTGTTTGA | AGACTGCTAC | AGTGAACTCA | CATACATATA | AATCTTAAAA | AAATAAAAGG | 11220 |
| CAATGAAACT | ATGATCCTGG | CCTTGAGCCT | TTTCTCAGTT | CTAACTGGTG | GTTGATATCA | 11280 |
| AATGAGACTG | CAGATGTGTG | GATGAATCTA | GCATAGATAA | GCAGTATTTT | TTTTTTAAGG | 11340 |
| TAGTGAGTAA | ATTCTAGCAT | AGATCTCATT | TTAAGGACTT | TGGGTGCAGT | GGGGCTCCGC | 11400 |
| AAAAAGGGAG | CAACAATAGT | CATATAGGCA | AAGGGCCTCA | AATGCTGCC | CCGTGGTCCA | 11460 |
| CAGATGGAAA | ACATACATGG | TCACCCATGA | ACTCTGCTGG | TCTCCTTATT | ACAGACTTAA | 11520 |
| TTCATATGGG | TGCTTACAGA | GGAATCCTAC | CAGACATCAC | ATATCAAATA | ACAAAGAGGC | 11580 |
| TTGATTTATT | GATGATTGGT | TGTTACAGAG | CACACAGCCT | GACTGGTGA | GGCTGGCTTT | 11640 |
| GACTGGGGAT | GCAATCGATG | CTTATAAACA | AACTAGGTCC | ATCAGAGCCA | GCGAGCTGCT | 11700 |

FIG.4H

```
GTCTTGTGGC TGRCCAGCTC TGTCTTCTAC TTGTGGTTCA GAGTTCTGTC TATTTCACAG    11760
TCATCTGGTT CTTCAGGATG AGCCCTTCTG TCAGACTCAT GAGCCTCACT TACCCAGCAT    11820
GTTACTTAGC CTTTTAATTT GGTCATCTCA TTCAATAATG TCCAGTTAAC TCATTCGCTA    11880
AATATCAAAT CCAAGAGGCG ATTGGTTTCA AAATGCCATA TTTATCTTCT ATTATAGAAT    11940
CAAGAGTTCT TTTTCCAGGG TTTTTAATTC CAGGTATTGT AAGAGCAAAT GAAACTGGTT    12000
TTTCAAATGG CTCTGAATGT GAACTGCTTC ACTGTGTTAT GTTATCCCTGT GCAGCTTGTA    12060
GGTTTTTACT TAGAGTCCTA GGGTCATTTC ATGATGTCCC AATTGTATGG TGTTGAGAAG    12120
AATATTCTAG TGATGTCTTT TTTTCTTAAA TGTCTTATTA AAGGTGGAAC CTCTGCTAGC    12180
CAGACAACTG TATTACTTTG CTCAACAAAA CACTGGACAT TTCCTGAGGG GCTACGAGTT    12240
ACCTGAACAC GTTACCACTC CAGATTACCA CCGCTCCCTC CGTCATTCTT CCATCCAAGA    12300
GTGAGAAGAA ATACTCTGAC AGGGCAGCCG GTTGCTGCCC TTTCTCTTTG GAAGAGCTAA    12360
GAAGTGAGTG GGTTTCCACT TGAAGACAAC AACAGGGCTT TGTGAGGAAA ACAGCTGTAT    12420
CTGCTCAACA GAGGAGCTTC CCCCAGAAGA GTGCCTGTCA GTCATCCAGG TCTTGACAAG    12480
TGCCAGGACT TGGGTGACTG TGCCCTGGCT TATAACTGTG AAACTTGATC CGAATTC       12537
```

FIG. 10A

```
ATGAACCTGG AGGGCGGCGG CCGAGGCGGA GAGTTCGGCA TGAGCGCGGT GAGCTGCGGC    60
AACGGGAAGC TCCGCCAGTG GCTGATCGAC CAGATCGACA GCGGCAAGTA CCCCGGGCTG   120
GTGTGGGAGA ACGAGGAGAA GAGCATCTTC CGCATCCCCT GGAAGCACGC GGGCAAGCAG   180
GACTACAACC GCGAGGAGGA CGCCGCGCTC TTCAAGGCTT GGGCACTGTT TAAAGGAAAG   240
TTCCGAGAAG GCATCGACAA GCCGGACCCT CCCACCTGGA AGACGCGCCT GCGGTGCGCT   300
TTGAACAAGA GCAATGACTT TGAGGAACTG GTTGAGCGGA GCCAGCTGGA CATCTCAGAC   360
CCGTACAAAG TGTACAGGAT TGTTCCTGAG GGAGCCAAAA AAGGAGCCAA GCAGCTCACC   420
CTGGAGACC CGCAGATGTC CATGAGCCAC CCCTACACCA TGACAACGCC TTACCCTTCG   480
CTCCCAGCCC AGTTCACAA CTACATGATG CCACCCCTCG ACCGAAGCTG GAGGGACTAC   540
GTCCCGGATC AGCCACACCC GGAAATCCCG TACCAATGTC CCATGACGTT TGGACCCCGC   600
GGCCACCACT GGCAAGGCCC AGCTTGTGAA AATGGTTGCC AGTGACAGG AACCTTTTAT   660
GCTTGTGCCC CACCTGAGTC CCAGGCTCCC GGAGTCCCCA CAGAGCCAAG CATAAGGTCT   720
```

FIG.10B

```
GCCGAAGCCT TGGCGTTCTC AGACTGCCGG CTGCACATCT GCCTGTACTA CCGGGAAATC     780
CTCGTGAAGG AGCTGACCAC GTCCAGCCCC GAGGGCTGCC GGATCTCCCA TGGACATACG     840
TATGACGCCA GCAACCTGGA CCAGGTCCTG TTCCCCTACC CAGAGGACAA TGGCCAGAGG     900
AAAAACATTG AGAAGCTGCT GAGCCACCTG GAGAGGGGCG TGGTCCTCTG GATGGCCCCC     960
GACGGGCTCT ATGCGAAAAG ACTGTGCCAG AGCAGGATCT ACTGGGACGG GCCCCTGGCG    1020
CTGTGCAACG ACCGGCCCAA CAAACTGGAG AGAGACCAGA CCTGCAAGCT CTTTGACACA    1080
CAGCAGTTCT TGTCAGAGCT GCAAGCGTTT GCTCACCACG GCCGCTCCCT GCCAAGATTC    1140
CAGGTGACTC TATGCTTTGG AGAGGAGTTT CCAGACCCTC AGAGGCAAAG AAAGCTCATC    1200
ACAGCTCACG TAGAACCTCT GCTAGCCAGA CAACTATATT ATTTTGCTCA ACAAAACAGT    1260
GGACATTTCC TGAGGGGCTA CGATTTACCA GAACACATCA GCAATCCAGA AGATTACCAC    1320
AGATCTATCC GCCATTCCTC TATTCAAGAA TGA                                 1353
```

FIG.11A

```
Met Asn Leu Glu Gly Gly Gly Arg Gly Glu Phe Gly Met Ser Ala
 1               5                  10                  15

Val Ser Cys Gly Asn Gly Lys Leu Arg Gln Trp Leu Ile Asp Gln Ile
                20                  25                  30

Asp Ser Gly Lys Tyr Pro Gly Leu Val Trp Glu Asn Glu Lys Ser
                35                  40                  45

Ile Phe Arg Ile Pro Trp Lys His Ala Gly Lys Gln Asp Tyr Asn Arg
                50                  55                  60

Glu Glu Asp Ala Ala Leu Phe Lys Ala Trp Ala Leu Phe Lys Gly Lys
 65                 70                  75                  80

Phe Arg Glu Gly Ile Asp Lys Pro Asp Pro Thr Trp Lys Thr Arg
                85                  90                  95

Leu Arg Cys Ala Leu Asn Lys Ser Asn Asp Phe Glu Glu Leu Val Glu
                100                 105                 110

Arg Ser Gln Leu Asp Ile Ser Asp Pro Tyr Lys Val Tyr Arg Ile Val
                115                 120                 125
```

FIG.11A-1

```
Pro Glu Gly Ala Lys Lys Gly Ala Lys Gln Leu Thr Leu Glu Asp Pro
130                 135                 140

Gln Met Ser Met Ser His Pro Tyr Thr Met Thr Thr Pro Tyr Pro Ser
145                 150                 155                 160

Leu Pro Ala Gln Val His Asn Tyr Met Pro Met Pro Pro Leu Asp Arg Ser
            165                 170                 175

Trp Arg Asp Tyr Val Pro Asp Gln Pro His Pro Glu Ile Pro Tyr Gln
            180                 185                 190

Cys Pro Met Thr Phe Gly Pro Arg Gly His His Trp Gln Gly Pro Ala
            195                 200                 205

Cys Glu Asn Gly Cys Gln Val Thr Gly Thr Phe Tyr Ala Cys Ala Pro
            210                 215                 220

Pro Glu Ser Gln Ala Pro Gly Val Pro Thr Glu Pro Ser Ile Arg Ser
225                 230                 235                 240

Ala Glu Ala Leu Ala Phe Ser Asp Cys Arg Leu His Ile Cys Leu Tyr
            245                 250                 255

Tyr Arg Glu Ile Leu Val Lys Glu Leu Thr Thr Ser Ser Pro Glu Gly
            260                 265                 270
```

FIG.11B

Cys Arg Ile Ser His Gly His Thr Tyr Asp Ala Ser Asn Leu Asp Gln
275                 280                 285

Val Leu Phe Pro Tyr Pro Glu Asp Asn Gly Gln Arg Lys Asn Ile Glu
290                 295                 300

Lys Leu Leu Ser His Leu Glu Arg Gly Val Val Leu Trp Met Ala Pro
305                 310                 315                 320

Asp Gly Leu Tyr Ala Lys Arg Leu Cys Gln Ser Arg Ile Tyr Trp Asp
325                 330                 335

Gly Pro Leu Ala Leu Cys Asn Asp Arg Pro Asn Lys Leu Glu Arg Asp
340                 345                 350

Gln Thr Cys Lys Leu Phe Asp Thr Gln Gln Phe Leu Ser Glu Leu Gln
355                 360                 365

Ala Phe Ala His His Gly Arg Ser Leu Pro Arg Phe Gln Val Thr Leu
370                 375                 380

FIG.11B-1

```
Cys Phe Gly Glu Glu Phe Pro Asp Pro Gln Arg Gln Arg Lys Leu Ile
385                     390                 395                 400

Thr Ala His Val Glu Pro Leu Leu Ala Arg Gln Leu Tyr Tyr Phe Ala
            405                 410                 415

Gln Gln Asn Ser Gly His Phe Leu Arg Gly Tyr Asp Leu Pro Glu His
        420                 425                 430

Ile Ser Asn Pro Glu Asp Tyr His Arg Ser Ile Arg His Ser Ser Ile
    435                 440                 445

Gln Glu
450
```

LSIRF POLYPEPTIDES

This application is a division of application Ser. No. 08/611,280, filed Apr. 3, 1996 now U.S. Pat. No. 5,891,666, which is a continuation-in-part of application Ser. No. 08/422,733, filed Apr. 14, 1995, abandoned, which are hereby incorporated by reference.

BACKGROUND

1. Field of the Invention

This invention relates to novel polypeptides having DNA binding activity, and to nucleic acid molecules encoding the polypeptides. The polypeptides, previously referred to as "IRF-3" polypeptides, are now referred to as "LSIRF" polypeptides (lymphocyte specific interferon regulatory factor), and are new members of the class of polypeptides known as interferon regulatory factors.

2. Description of Related Art

Regulation of gene expression can occur at several different levels, but the activation of gene-specific transcription factors is considered the most fundamental to this process. One family of transcription factors, the interferon regulatory factors (IRFs), consists of four members: IRF-1, IRF-2, ISGF3γ, and ICSBP. All four IRFs are characterized by a strongly conserved, N-terminal DNA-binding domain containing a repeated tryptophan motif (Veals et al., (Mol. Cell. Biol., 12:3315–3324 [1992]).

Interferon regulatory factors-1 (IRF-1) and -2 (IRF-2) were originally identified by studies of the transcriptional regulation of the human interferon-beta (IFN-β) gene (Miyamoto et al., Cell, 54:903–913 [1988]) and (Harada et al., Cell, 58:729–739 [1989]). cDNA expression studies have demonstrated that IRF-1 functions as a transcriptional activator of IFN and IFN-inducible genes, whereas IRF-2 represses the effect of IRF-1 (Fujita et al., Nature, 337:270–272 [1989]) and (Harada et al., Cell, 63:303–312 [1990]). Recent analyses have shown that IRF-1 can also act as a tumor suppressor gene and IRF-2 as a possible oncogene (Harada et al, Science, 259:971–974 [1993]). IRF-1 expression is induced by type-I (α/β) and type-II (γ) IFNs (Miyamoto et al., Cell, 54:903–913 [1988]; Kanno et al., Mol. Cell Biol., 13:3951–3963 [1993]), whereas IRF-2 is both constitutively expressed and induced by type-I IFNs (Harada et al., Cell, 58:729–739 [1989]).

Interferon-stimulated gene factor-3 gamma (ISGF3γ) is an IFN-γ-inducible protein which associates with ISGF3α subunits activated from a latent cytosolic form by type-I IFNs (Levy et al, EMBO J., 9:1105–1111 [1990]; Levy et al., New Biologist, 2:383–392 [1990]). Upon association, this complex has been shown to translocate to the nucleus and bind a specific DNA sequence found in the promoter region of IFN-inducible genes, known as the ISRE (IFN-stimulated response element; Veals et al., Mol. Cell. Biol., 12:3315–3324 [1992]). Recently, ISGF3α subunits of 91/84 kDa and 113 kDa have been cloned (Schindler et al, Proc. Natl. Acad. Sci. USA, 89:7836–7839 [1992]; Fu et al, Proc. Natl. Acad. Sci. USA, 89:7840–7843 [1992]) and designated as signal transducer and activator of transcription-1 (Stat-1) and -2 (Stat-2), respectively, which are targets of JAK kinase phosphorylation following type-I IFN/IFN-receptor engagement (Shuai et al, Science, 261:1744–1746 [1993]; Darnell et al, Science, 261:1415–1421 [1994]).

Interferon consensus sequence binding protein (ICSBP) is also an IFN-γ-inducible protein, originally isolated as a protein that recognizes the ISRE motif (also called ICS) of the promoter of murine MHC class I, H-2L$^D$ gene (Driggers et al, Proc. Natl. Acad. Sci. USA, 87:3743–3747 [1990]). However, unlike IRF-1, IRF-2, and ISGF3γ, ICSBP exhibits a tissue-restricted pattern of expression, as it is induced exclusively in cells of macrophage and lymphoid lineages (Driggers et al, Proc. Natl. Acad. Sci. USA, 87:3743–3747 [1990]). Recent studies have suggested that ICSBP has a similar role to IRF-2 in antagonizing the effect of IRF-1 on the induction of IFN and IFN-inducible genes (Weisz et al., J. Biol. Chem., 267:25589–25596 [1992]; Nelson et al., Mol. Cell. Biol., 13:588–599 [1993]). The ISREs of interferon-inducible genes overlap IRF-E, the DNA sequences recognized by IRF-1 and -2 (Tanaka et al., Mol Cell. Biol. 13:4531–4538 [1993]). Very recently, ISGF3γ was shown to bind the IRF-Es of the IFN-β gene (Kawakami et al., FEBS Letters, 358:225–229 [1995]).

In view of the importance of IRFs in regulating the expression of the interferon genes and other genes, there is a need in the art to identify other IRFs, especially tissue specific IRFs.

Accordingly, it is an object of this invention to identify novel members of the IRF gene family.

Other objects will be readily apparent to one of ordinary skill in the art.

SUMMARY OF THE INVENTION

The present invention provides novel nucleic acid molecules encoding a lymphocyte specific interferon regulatory factor. The molecules, which were previously referred to as "IRF-3" molecules, are now referred to as "LSIRF" molecules, however this term may be used interchangeably with the term "LSIRF" molecules.

In one aspect, the present invention provides an isolated nucleic acid molecule encoding a LSIRF polypeptide or fragment thereof, selected from the group consisting of:

a) a nucleic acid molecule having a nucleotide sequence of SEQ. ID. NO: 1;

b) a nucleic acid molecule having a nucleotide sequence of SEQ. ID. NO: 4;

c) a nucleic acid molecule having a nucleotide sequence of SEQ. ID. NO: 24 or the "Double Q" variant thereof;

d) a nucleic acid molecule having a nucleotide sequence encoding the amino acid sequence of SEQ. ID. NO: 2;

e) a nucleic acid molecule having a nucleotide sequence encoding the amino acid sequence of SEQ. ID. NO: 25 or the "Double Q" variant thereof; and f) a nucleic acid molecule having a nucleotide sequence which hybridizes with the nucleic acid molecule of (a), (b), (c), (d), (e), or with a fragment thereof.

The invention further provides a polypeptide that is the product of the expression of these nucleic acid molecules in a host cell.

Still further, the invention provides an antibody specifically binding the LSIRF polypeptide. Optionally, the antibody is a monoclonal antibody.

In another aspect, the invention provides an isolated polypeptide or fragment thereof having the specific DNA binding activity of a LSIRF polypeptide.

In another aspect, the present invention provides a vector comprising a DNA molecule encoding a LSIRF polypeptide.

In still another aspect, the invention provides a host cell stably transformed or transfected with a vector comprising a DNA molecule encoding a LSIRF polypeptide.

In yet another aspect, the invention provides an isolated LSIRF polypeptide or fragment thereof; the polypeptide may have the amino acid sequence of SEQ ID NO: 2.

In a further aspect, the invention provides a LSIRF polypeptide that is the product of a prokaryotic or eukaryotic host cell expression of an exogenous LSIRF nucleic acid sequence.

The invention further provides a method of producing a LSIRF polypeptide comprising culturing a prokaryotic or eukaryotic host cell under conditions that permit LSIRF expression.

BRIEF DESCRIPTION OF THE DRAWINGS

FIGS. 1A–1B depicts a mouse full length LSIRF cDNA nucleic acid sequence (SEQ ID NO: (SEQ ID NO:1).

FIGS. 2A-1–2B-1 depicts a mouse full length LSIRF polypeptide amino acid sequence (SEQ ID NO: (SEQ ID NO:2).

FIGS. 3A–3B depicts a mouse LSIRF gene 5' flanking sequence (SEQ ID NO: (SEQ ID NO:3).

FIGS. 4A–4H depicts a mouse LSIRF genomic DNA sequence (SEQ ID NO: (SEQ ID NO:4).

FIGS. 10A–10B depicts the full length nucleotide sequence of the coding region of human LSIRF in the "Single Q" form. (SEQ. ID. NO.: 24). The "Double Q" form has an additional codon encoding the amino acid Q (Glu) inserted between the codons for amino acid 163 and amino acid 164.

FIGS. 11A–11B-1 depicts the putative "Single Q" form of the amino acid sequence of human LSIRF (SEQ. ID. NO.: 25), as translated from the nucleotide Sequence of FIG. 10. The "Double Q" form has an additional amino acid Q (Glu) inserted between amino acid 163 and amino acid 164.

DETAILED DESCRIPTION OF THE INVENTION

Figure 5:
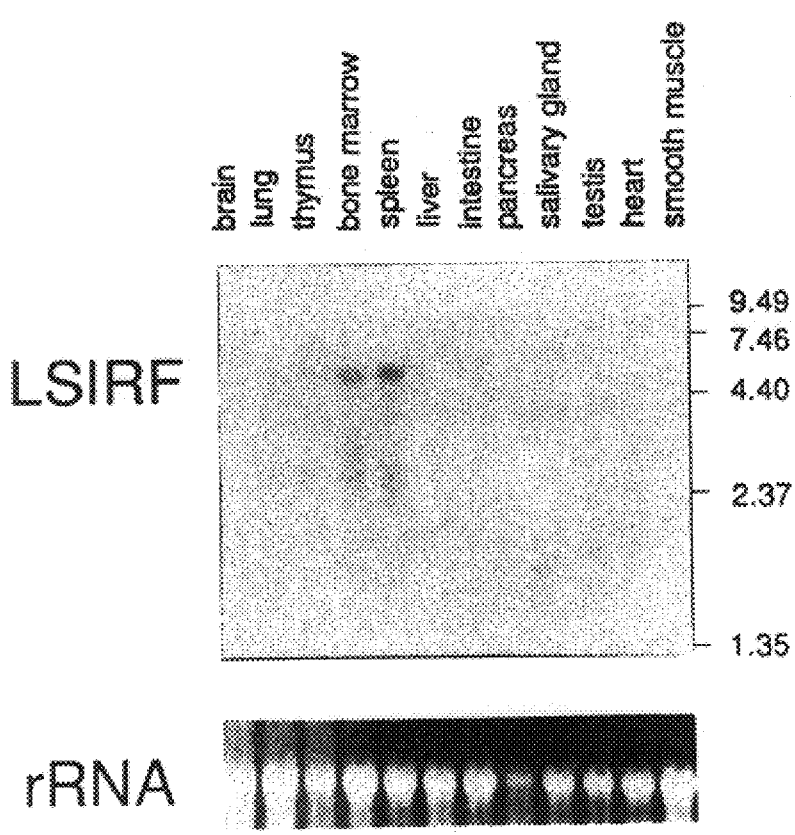
FIG. 5 depicts a Northern blot of RNA from various tissues of a mouse. The blot was probed with a radio-labeled LSIRF probe to identify LSIRF transcripts. RNA base pair markers indicating the size of the transcripts are indicated on the left. A photo of an agarose gel indicating ribosomal RNA is also shown.

The terms "IRF-3" and "LSIRF" are used interchangeably herein and refer to the same nucleic acid and amino acid sequences; both the "Single Q" and "Double Q" forms of LSIRF are included in this definition (see Example 5).

As used herein, the term "biologically active" refers to a full length polypeptide or fragment thereof derived from any source, that binds ISRE (interferon stimulated response element) type DNA fragments such as murine MHCI ISRE, human ISG54, and/or ISRE mutants such as ISREm1 or ISREm4 (the sequences of which are set forth in Table 1). Biologically active polypeptides or fragments thereof also include those polypeptides or fragments that have immunological cross reactivity with an antibody (polyclonal or monoclonal) that is raised against, and reacts with, a full length LSIRF polypeptide such as the LSIRF polypeptides set forth in FIGS. 2 and 25.

As used herein, the term "stably transformed or transfected" refers to a nucleic acid molecule that has been inserted into a host cell and exists in the host cell, either as a part of the host cell genomic DNA or as an independent molecule (e.g., extra-chromosomally), and that is maintained and replicated in the parent host cell so that it is passed down through successive generations of the host cell.

The term "synthetic DNA" refers to a nucleic acid molecule produced in whole or in part by chemical synthesis methods.

The term "vector" refers to a nucleic acid molecule amplification, replication, and/or expression vehicle in the form of a plasmid or viral DNA system where the plasmid or viral DNA may be functional with bacterial, yeast, invertebrate, and/or mammalian host cells. The vector may remain independent of host cell genomic DNA or may integrate in whole or in part with the genomic DNA. The vector will contain all necessary elements so as to be functional in any host cell it is compatible with. Such elements are set forth below.

One aspect of the present invention provides methods of preparing a LSIRF polypeptide. Typically, the polypeptide will be prepared by obtaining a nucleic acid molecule encoding the polypeptide, inserting this nucleic acid molecule into a suitable expression vector, inserting the vector into a compatible host cell, expressing the LSIRF polypeptide in the host cell, and purifying the LSIRF polypeptide.

1. Preparation of DNA Encoding LSIRF Polypeptides

A nucleic acid molecule encoding LSIRF can readily be obtained in a variety of ways, including, without limitation, chemical synthesis, cDNA or genomic library screening, expression library screening, and/or PCR amplification of cDNA. These methods and others useful for isolating such DNA are set forth, for example, by Sambrook et al. (*Molecular Cloning: A Laboratory Manual*, Cold Spring Harbor Laboratory Press, Cold Spring Harbor, N.Y. [1989]), by Ausubel et al., eds. (*Current Protocols in Molecular Biology*, Current Protocols Press [1994]), and by Berger and Kimmel (*Methods in Enzymology: Guide to Molecular Cloning Techniques*, vol. 152, Academic Press, Inc., San Diego, Calif. [1987]). Preferred nucleic acid sequences encoding LSIRF are mammalian sequences. Most preferred nucleic acid sequences encoding LSIRF are human, rat, and mouse.

Chemical synthesis of a LSIRF nucleic acid molecule can be accomplished using methods well known in the art, such as those set forth by Engels et al. (*Angew. Chem. Intl. Ed.*, 28:716–734 [1989]). These methods include, inter alia, the phosphotriester, phosphoramidite and H-phosphonate methods of nucleic acid synthesis. Typically, the nucleic acid molecule encoding the full length LSIRF polypeptide will be several hundred base pairs (bp) or nucleotides in length. Nucleic acids larger than about 100 nucleotides in length can be synthesized as several fragments, each fragment being up to about 100 nucleotides in length. The fragments can then be ligated together, as described below, to form a full length nucleic acid encoding the LSIRF polypeptide. A preferred method is polymer-supported synthesis using standard phosphoramidite chemistry.

Alternatively, the nucleic acid encoding a LSIRF polypeptide may be obtained by screening an appropriate cDNA library (i.e., a library prepared from one or more tissue source(s) believed to express the polypeptide) or a genomic library (a library prepared from total genomic DNA). The source of the cDNA library is typically a tissue from any species that is believed to express LSIRF in reasonable quantities (such as lymphoid tissue). The source of the genomic library may be any tissue or tissues from any mammalian or other species believed to harbor a gene encoding LSIRF or a LSIRF homologue. The library can be screened for the presence of the LSIRF cDNA/gene using one or more nucleic acid probes (oligonucleotides, cDNA or genomic DNA fragments that possess an acceptable level of homology to the LSIRF or LSIRF homologue cDNA or gene to be cloned) that will hybridize selectively with LSIRF or LSIRF homologue cDNA(s) or gene(s) that is(are) present in the library. The probes typically used for such library screening usually encode a small region of the LSIRF DNA sequence from the same or a similar species as the species from which the library was prepared. Alternatively, the probes may be degenerate, as discussed below.

Library screening is typically accomplished by annealing the oligonucleotide probe or cDNA to the clones in the library under conditions of stringency that prevent non-specific binding but permit binding of those clones that have a significant level of homology with the probe or primer. Typical hybridization and washing stringency conditions depend in part on the size (i.e., number of nucleotides in length) of the cDNA or oligonucleotide probe, and whether the probe is degenerate. The probability of obtaining a clone(s) is also considered in designing the hybridization solution (i.e., whether a cDNA or genomic library is being screened; if it is a cDNA library, the probability that the cDNA of interest is present at a high level).

Where DNA fragments (such as cDNAs) are used as probes, typical hybridization conditions are those for example as set forth in Ausubel et al., eds., supra. After hybridization, the blot containing the library is washed at a suitable stringency, depending on several factors such as probe size, expected homology of probe to clone, type of library being screened, number of clones being screened, and the like. Examples of stringent washing solutions (which are usually low in ionic strength and are used at relatively high temperatures) are as follows. One such stringent wash is 0.015 M NaCl, 0.005 M NaCitrate and 0.1 percent SDS at 55–65° C. Another such stringent buffer is 1 mM $Na_2EDTA$, 40 mM NaHPO4, pH 7.2, and 1 percent SDS at about 40–50° C. One other stringent wash is 0.2× SSC and 0.1 percent SDS at about 50–65° C.

Where oligonucleotide probes are used to screen cDNA or genomic libraries, two protocols for stringent washing conditions as follows may be used, for example. The first protocol uses 6×SSC with 0.05 percent sodium pyrophosphate at a temperature of between about 35 and 62° C., depending on the length of the probe. For example, 14 base probes are washed at 35–40° C., 17 base probes at 45–50° C., 20 base probes at 52–57° C., and 23 base probes at 57–63° C. The temperature can be increased 2–3° C. where the background non-specific binding appears high. A second protocol uses tetramethylammonium chloride (TMAC) for washing. One such stringent washing solution is 3 M TMAC, 50 mM Tris-HCl, pH 8.0, and 0.2 percent SDS. The washing temperature using this solution is a function of the length of the probe. For example, a 17 base probe is washed at about 45–50° C.

Another suitable method for obtaining a nucleic acid encoding a LSIRF polypeptide is the polymerase chain reaction (PCR). In this method, poly(A)+RNA or total RNA is extracted from a tissue that expresses LSIRF (such as lymphoid tissue). cDNA is then prepared from the RNA using the enzyme reverse transcriptase. Two primers typically complementary to two separate regions of the LSIRF cDNA (oligonucleotides) are then added to the cDNA along with a polymerase such as Taq polymerase, and the polymerase amplifies the cDNA region between the two primers.

Where the method of choice for preparing the nucleic acid encoding the LSIRF polypeptide requires the use of oligonucleotide primers or probes (e.g. PCR, cDNA or genomic library screening), the oligonucleotide sequences selected as probes or primers should be of adequate length and sufficiently unambiguous so as to minimize the amount of non-specific binding that will occur during library screening or PCR amplification. The actual sequence of the probes or primers is usually based on conserved or highly homologous sequences or regions from the same or a similar gene from another organism. Optionally, the probes or primers can be fully or partially degenerate, i.e., contain a mixture of probes/primers, all encoding the same amino acid sequence, but using different codons to do so. An alternative to preparing degenerate probes is to place an inosine in some or all of those codon positions that vary by species. The oligonucleotide probes or primers may be prepared by chemical synthesis methods for DNA as described above.

LSIRF mutant or variant sequences are contemplated as within the scope of the present invention. A mutant or variant sequence as used herein is a sequence that contains one or more nucleotide substitutions, deletions, and/or insertions as compared to the wild type sequence that result in amino acid sequence variations as compared to the wild type amino acid sequence. In some cases, naturally occurring LSIRF amino acid mutants or variants may exist, due to the existence of natural allelic variation. Such naturally occurring variants are also within the scope of the present invention. Preparation of synthetic mutant sequences is well known in the art, and is described for example in Wells et al. (Gene, 34:315 [1985]), and in Sambrook et al, supra.

2. Preparation of a LSIRF Polypeptide 5' Flanking Sequence

Included within the scope of the present invention are LSIRF 5' flanking sequences (also referred to herein as "promoters") from any species. By promoter as used herein is meant the 5' flanking sequence of a LSIRF gene. The 5' flanking sequence may have various transcription factor binding sites, and also may possess a TATA box at about position −30, and a CCAAT box upstream from the TATA box. Such 5' flanking sequences are characterized as naturally regulating the transcription of a LSIRF gene in vivo, either alone or in combination with other factors such a enhancer elements, repressors, and the like (any or all of which may be very distally located). Preferred 5' flanking sequences are mammalian LSIRF 5' flanking sequences. Most preferred are human LSIRF 5' flanking sequences.

The 5' flanking sequences of the present invention may be obtained from genomic libraries by screening the library with cDNAs or genomic LSIRF fragments that preferably hybridize to the 5' portion of the LSIRF gene. Such fragments may hybridize to a clone in the library that contains some or all of the LSIRF 5' flanking sequence, which is generally located just 5' to the start of the coding sequence for LSIRF. Where the identified clone contains only a portion of the promoter, the clone itself, or a fragment of it, may be used for subsequent rounds of genomic library screening to obtain additional 5' flanking sequence. Screening with the fragments (including hybridization and washing) may be accomplished as described above for cloning a LSIRF gene and/or cDNA.

3. Preparation of a Vector for LSIRF Expression

After cloning, the cDNA or gene encoding a LSIRF polypeptide or fragment thereof has been isolated, it is typically inserted into an amplification and/or expression vector in order to increase the copy number of the gene and/or to express the polypeptide in a suitable host cell. The vector is often a commercially available vector, though "custom made" vectors may be used as well. The vector is selected to be functional in the particular host cell employed (i.e., the vector is compatible with the host cell machinery such that amplification of the LSIRF gene and/or expression of the gene can occur). The LSIRF polypeptide or fragment thereof may be amplified/expressed in prokaryotic, yeast, insect (baculovirus systems) and/or eukaryotic host cells. Selection of the host cell will depend at least in part on whether the LSIRF polypeptide or fragment thereof is to be glycosylated. If so, yeast, insect, or mammalian host cells are preferable; yeast cells will glycosylate the polypeptide, and insect and mammalian cells can glycosylate and/or phosphorylate the polypeptide as it naturally occurs on the LSIRF polypeptide (i.e., "native" glycosylation and/or phosphorylation).

Typically, the vectors used in any of the host cells will contain 5' flanking sequence and other regulatory elements as well such as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Optionally, the vector may contain a "tag" sequence, i.e., an oligonucleotide sequence located at the 5' or 3' end of the LSIRF coding sequence that encodes polyHis (such as hexaHis) or another small immunogenic sequence. This tag will be expressed along with the protein, and can serve as an affinity tag for purification of the LSIRF polypeptide from the host cell. Optionally, the tag can subsequently be removed from the purified LSIRF polypeptide by various means such as using a selected peptidase for example.

A. 5' Flanking Sequence Element

The 5' flanking sequence may be homologous (i.e., from the same species and/or strain as the host cell), heterologous (i.e., from a species other than the host cell species or strain), hybrid (i.e., a combination of p5' flanking sequences from more than one source), synthetic, or it may be the native LSIRF 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by, the host cell machinery.

The 5' flanking sequences useful in the vectors of this invention may be obtained by any of several methods well known in the art. Typically, 5' flanking sequences useful herein other than the LSIRF 5' flanking sequence will have been previously identified by mapping and/or by restriction endonuclease digestion and can thus be isolated from the proper tissue source using the appropriate restriction endonucleases. In some cases, the full nucleotide sequence of the 5' flanking sequence may be known. Here, the 5' flanking sequence may be synthesized using the methods described above for nucleic acid synthesis or cloning.

Where all or only portions of the 5' flanking sequence are known, it may be obtained using PCR and/or by screening a genomic library with suitable oligonucleotide and/or 5' flanking sequence fragments from the same or another species.

Where the 5' flanking sequence is not known, a fragment of DNA containing the some 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column or other methods known to the skilled artisan. Selection of suitable enzymes to accomplish this purpose will be readily apparent to one of ordinary skill in the art.

B. Origin of Replication Element

This component is typically a part of prokaryotic expression vectors purchased commercially, and aids in the amplification of the vector in a host cell. Amplification of the vector to a certain copy number can, in some cases, be important for optimal expression of the LSIRF polypeptide. If the vector of choice does not contain an origin of replication site, one may be chemically synthesized based on a known sequence, and ligated into the vector.

C. Transcription Termination Element

This element is typically located 3' to the end of the LSIRF polypeptide coding sequence and serves to terminate transcription of the LSIRF polypeptide. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those described above.

D. Selectable Marker(s) Element

Selectable marker genes encode proteins necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

E. Ribosome Binding Site Element

This element, commonly called the Shine-Dalgarno sequence (prokaryotes) or the Kozak sequence (eukaryotes), is necessary for translation initiation of mRNA. The element is typically located 3' to the promoter and 5' to the coding sequence of the polypeptide to be synthesized. The Shine-Dalgarno sequence is varied but is typically a polypurine (i.e., having a high A-G content). Many Shine-Dalgarno sequences have been identified, each of which can be readily synthesized using methods set forth above.

All of the elements set forth above, as well as others useful in this invention, are well known to the skilled artisan and are described, for example, in Sambrook et al. (*Molecular Cloning:A Laboratory Manual*, Cold Spring Harbor Laboratory Press, Cold Spring Harbor, N.Y. [1989]) and Berger et al., eds. (*Guide to Molecular Cloning Techniques*, Academic Press, Inc., San Diego, Calif. [1987]).

F. Signal Sequence Element

For those embodiments of the invention where the transgene is to be secreted, a signal sequence, is frequently present to direct the polypeptide encoded by the transgene out of the cell where it is synthesized. Typically, the signal sequence is positioned in the coding region of the transgene towards or at the 5' end of the coding region. Many signal sequences have been identified, and any of them that are functional in the transgenic tissue may be used in conjunction with the transgene. Therefore, the signal sequence may be homologous or heterologous to the transgene, and may be homologous or heterologous to the transgenic mammal. Additionally, the signal sequence may be chemically synthesized using methods set forth above. However, for purposes herein, preferred signal sequences are those that occur naturally with the transgene (i.e., are homologous to the transgene).

G. Intron Element

In many cases, transcription of the transgene is increased by the presence of one or more introns on the vector. The intron may be naturally occurring within the transgene sequence, especially where the transgene is a full length or a fragment of a genomic DNA sequence. Where the intron is not naturally occurring within the DNA sequence (as for most cDNAs), the intron(s) may be obtained from another source. The intron may be homologous or heterologous to the transgene and/or to the transgenic mammal. The position of the intron with respect to the promoter and the transgene is important, as the intron must be transcribed to be effective. As such, where the transgene is a cDNA sequence, the preferred position for the intron is 3' to the transcription start site, and 5' to the polyA transcription termination sequence. Preferably for cDNA transgenes, the intron will be located on one side or the other (i.e., 5' or 3') of the transgene sequence such that it does not interrupt the transgene sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

H. Construction of Vectors

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

The final vectors used to practice this invention are typically constructed from a starting vectors such as a commercially available vector. This vector may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

One other method for constructing the vector to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion.

Preferred vectors for practicing this invention are those which are compatible with bacterial, insect, and mammalian host cells. Such vectors include, inter alia, pCRII (Invitrogen Company, San Diego, Calif.), pBSII (Stratagene Company, LaJolla, Calif.), and pETL (BlueBacII; Invitrogen).

After the vector has been constructed and a LSIRF nucleic acid has been inserted into the proper site of the vector, the completed vector may be inserted into a suitable host cell for amplification and/or LSIRF polypeptide expression. The host cells typically used include, without limitation: Prokaryotic cells such as gram negative or gram positive cells, i.e., any strain of *E. coli*, Bacillus, Streptomyces, Saccharomyces, Salmonella, and the like; eukaryotic cells such as CHO (Chinese hamster ovary) cells, human kidney 293 cells, COS-7 cells; insect cells such as Sf4, Sf5, Sf9, and Sf21 and High 5 (all from the Invitrogen Company, San Diego, Calif.); and various yeast cells such as Saccharomyces and Pichia.

Insertion (also referred to as "transformation" or "transfection") of the vector into the selected host cell may be accomplished using such methods as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook et al., supra.

The host cells containing the vector (i.e., transformed or transfected) may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

4. Evaluation of Expression

The amount of LSIRF polypeptide produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

5. Purification of the LSIRF polypeptide

If the LSIRF polypeptide has been designed to be secreted from the host cells, the majority of polypeptide will likely be found in the cell culture medium. If however, the LSIRF polypeptide is not secreted from the host cells, it will be present in the cytoplasm (for eukaryotic, gram positive bacteria, and insect host cells) or in the periplasm (for gram negative bacteria host cells).

For intracellular LSIRF, the host cells are first disrupted mechanically or osmotically to release the cytoplasmic contents into a buffered solution. LSIRF polypeptide is then isolated from this solution.

Purification of LSIRF polypeptide from solution can be accomplished using a variety of techniques. If the polypeptide has been synthesized such that it contains a tag such as Hexahistidine (LSIRF/hexaHis) or other small peptide at either its carboxyl or amino terminus, it may essentially be purified in a one-step process by passing the solution through an affinity column where the column matrix has a high affinity for the tag or for the polypeptide directly (i.e., a monoclonal antibody specifically recognizing LSIRF). For example, polyhistidine binds with great affinity and specificty to nickel, thus an affinity column of nickel (such as the Qiagen nickel columns) can be used for purification of LSIRF/polyHis. (See for example, Ausubel et al., eds., *Current Protocols in Molecular Biology*, Section 10.11.8, John Wiley & Sons, New York [1993]).

Where the LSIRF polypeptide has no tag and no antibodies are available, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity. Preferred methods for purification include polyHistidine tagging and ion exchange chromatography in combination with preparative isoelectric focusing.

If it is anticipated that the LSIRF polypeptide will be found primarily in the periplasmic space of the bacteria or the cytoplasm of eukaryotic cells, the contents of the periplasm or cytoplasm, including inclusion bodies (bacteria) if the processed polypeptide has formed such complexes, can be extracted from the host cell using any standard technique known to the skilled artisan. For example, the host cells can be lysed to release the contents of the periplasm by French press, homogenization, and/or sonication. The homogenate can then be centrifuged.

If the LSIRF polypeptide has formed inclusion bodies in the periplasm, the inclusion bodies can often bind to the inner and/or outer cellular membranes and thus will be found primarily in the pellet material after centrifugation. The pellet material can then be treated with a chaotropic agent such as guanidine or urea to release, break apart, and solubilize the inclusion bodies. The LSIRF polypeptide in its now soluble form can then be analyzed using gel electrophoresis, immunoprecipitation or the like. If it is desired to isolate the LSIRF polypeptide, isolation may be accomplished using standard methods such as those set forth below and in Marston et al. (Meth. Enz., 182:264–275 [1990]).

If LSIRF polypeptide inclusion bodies are not formed to a significant degree in the periplasm of the host cell, the LSIRF polypeptide will be found primarily in the supernatant after centrifugation of the cell homogenate, and the LSIRF polypeptide can be isolated from the supernatant using methods such as those set forth below.

In those situations where it is preferable to partially or completely isolate the LSIRF polypeptide, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

The term "substance" as used herein refers to compounds useful in inhibiting either transcription of the LSIRF gene, translation of the LSIRF mRNA, or activity of the LSIRF polypeptide.

The term "therapeutically effective" refers to the amount of the substance that is required in order to obtain the desired physiological response, i.e., to suppress the activation of lymphocytes in response to an antigen stimulus or autoimmune response, or increase lymphocyte number to stimulate the immune response to an antigen stimulus.

The term "antigen stimulus" refers to a compound that is either found naturally in a mammal (endogenous) and elicits some aspect of the immune response, or is from an exogenous source and invades the mammal's system and elicits some aspect(s) of the immune response.

The compositions useful for practicing the methods of the present invention may be prepared according to standard methods well known by those of ordinary skill in the art.

Therapeutic Anti-LSIRF Antibodies

Polyclonal or monoclonal therapeutic anti-LSIRF antibodies useful in practicing this invention may be prepared in laboratory animals or by recombinant DNA techniques using the following methods. Polyclonal antibodies to the LSIRF molecule or a fragment thereof containing the target amino acid sequence generally are raised in animals by multiple subcutaneous (sc) or intraperitoneal (ip) injections of the LSIRF molecule in combination with an adjuvant such as Freund's adjuvant (complete or incomplete). To enhance immunogenicity, it may be useful to first conjugate the LSIRF molecule or a fragment containing the target amino acid sequence of to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N$=C=NR, where R and $R^1$ are different alkyl groups. Alternatively, LSIRF-immunogenic conjugates can be produced recombinantly as fusion proteins.

Animals are immunized against the immunogenic LSIRF conjugates or derivatives (such as a fragment containing the target amino acid sequence) by combining about 1 mg or about 1 μg of conjugate (for rabbits or mice, respectively) with about 3 volumes of Freund's complete adjuvant and injecting the solution intradermally at multiple sites. Approximately 7 to 14 days later, animals are bled and the serum is assayed for anti-LSIRF titer. Animals are boosted with antigen repeatedly until the titer plateaus. Preferably, the animal is boosted with the same LSIRF molecule or fragment thereof as was used for the initial immunization, but conjugated to a different protein and/or through a different cross-linking agent. In addition, aggregating agents such as alum are used in the injections to enhance the immune response.

Monoclonal antibodies may be prepared by recovering spleen cells from immunized animals and immortalizing the cells in conventional fashion, e.g. by fusion with myeloma cells. The clones are then screened for those expressing the desired antibody. The monoclonal antibody preferably does not cross-react with other LSIRF polypeptides or LSIRF polypeptide isoforms.

Preparation of antibodies using recombinant DNA methods such as the phagemid display method, may be accomplished using commercially available kits, as for example, the Recombinant Phagemid Antibody System available from Pharmacia (Uppsala, Sweden), or the SurfZAP™ phage display system (Stratagene Inc., La Jolla, Calif.).

Preferably, antibodies for administration to humans, although prepared in a laboratory animal such as a mouse, will be "humanized", or chimeric, i.e. made to be compatible with the human immune system such that a human patient will not develop an immune response to the antibody. Even more preferably, human antibodies which can now be prepared using methods such as those described for example in Lonberg et al. (Nature Genetics, 7: 13–21 [1994]) are preferred for therapeutic administration to patients.

Antibodies produced using any of the above described methods can be conjugated to compounds that are able to penetrate the cell membrane and the nuclear membrane for import of the antibody into the nucleus using, for example, a nuclear targeting signal such as that found on the phosphorylated form of LSIRF.

Therapeutic Compositions and Administration

Therapeutic formulations of the compositions useful for practicing the present invention such as LSIRF antibodies may be prepared for storage by mixing the selected composition having the desired degree of purity with optional physiologically acceptable carriers, excipients, or stabilizers (Remington's Pharmaceutical Sciences, 18th edition, A. R. Gennaro, ed., Mack Publishing Company [1990]) in the form of a lyophilized cake or an aqueous solution. Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The composition to be used for in vivo administration must be sterile. This is readily accomplished by filtration through sterile filtration membranes, prior to or following lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle.

The route of administration of the composition is in accord with known methods, e.g. oral, injection or infusion by intravenous, intraperitoneal, intracerebral, intramuscular, intraocular, intraarterial, or intralesional routes, or by sustained release systems or implantation device. Where desired, the compositions may be administered continuously by infusion, bolus injection or by implantation device.

Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al, Biopolymers, 22: 547–556 [1983]), poly (2-hydroxyethyl-methacrylate) (Langer et al., J. Biomed. Mater. Res., 15: 167–277 [1981] and Langer, Chem. Tech., 12: 98–105 [1982]), ethylene vinyl acetate (Langer et al., supra) or poly-D(−)-3-hydroxybutyric acid (EP 133,988). Sustained-release compositions also may include liposomes, which can be prepared by any of several methods known in the art (e.g., DE 3,218,121; Epstein et al., Proc. Natl. Acad. Sci. USA, 82: 3688–3692 [1985]; Hwang et al., Proc. Natl. Acad. Sci. USA, 77: 4030–4034 [1980]; EP 52,322; EP 36,676; EP 88,046; EP 143,949).

An effective amount of the compositions to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage may range from about 1 [[g]mg/kg to up to 100 mg/kg or more, depending on the factors mentioned above. Typically, a clinician will administer the composition until a dosage is reached that achieves the desired effect. The progress of this therapy is easily monitored by conventional assays designed to evaluate.

The LSIRF nucleic acid molecules, 5' flanking sequences, polypeptides, and antibodies of the present invention will have a variety of uses that are readily apparent to one of ordinary skill in the art.

The LSIRF polypeptides will have utility as a target for therapeutic compounds used to regulate lymphocyte activation. By blocking either the expression of the LSIRF gene (via decreasing LSIRF transcription or translation) or the activity of the LSIRF polypeptide, it is possible to suppress lymphocyte activation in response to certain environmental stimuli. By increasing the level of expression of the LSIRF gene (via up-regulation of the LSIRF 5' flanking sequence), it is possible to stimulate lymphocyte activation and proliferation, thereby increasing the immune response to particular antigens.

The antibodies of the present invention may be polyclonal or monoclonal, and may be raised against LSIRF from any mammal. These antibodies can be used to assess the presence and/or amount of LSIRF polypeptide in a given tissue or biological sample. In addition, they may be used to block the activity of LSIRF by binding to the active site of this polypeptide. Thus, the antibodies themselves may find use as therapeutic compounds to decrease the level of LSIRF polypeptide.

The invention may be more readily understood by reference to the following Examples. These Examples should not be construed in any way as limiting the scope of the invention.

EXAMPLES

Example 1

Cloning the Mouse LSIRF cDNA

Two PCR (polymerase chain reaction) partially degenerate primers were used for PCR amplification of cDNA prepared from total RNA obtained from spleen tissue of a C57Bl/6 mouse. The primers were:

ATCCTGGAACACGC (SEQ ID NO:5)
GCACACGAACTGCCTTCCA (SEQ ID NO:6)

Primer No. 5 contained three inosine bases which were located between nucleotides 2 and 3 (T and C), nucleotides 4 and 5 (C and T), and nucleotides 9 and 10 (A and C). Primer No. 6 contained four inosine bases in the sequence which were located between nucleotides 5 and 6 (A and C), nucleotides 7 and 8 (G and A), nucleotides 9 and 10 (A and C), and nucleotides 11 and 12 (T and G).

PCR was carried out on a programmable thermal cycler (Perkin-Elmer Cetus, Norwalk, Conn.) in 50 μl of PCR buffer (10 mM Tris-HCl pH 8.3, 1.5 mM $MgCl_2$, and 50 mM KCl) containing 200 μM dNTPs, 2 U Taq polymerase, and 100 pM of each primer. Thirty cycles of PCR were performed under the following temperature regime: 94° C. for 60 seconds; 37° C. for 60 seconds; and 72° C. for 60 seconds. The PCR products were subsequently inserted directly into the pCRII plasmid using the TA-Cloning System (Invitrogen Corp., San Diego, Calif.). The plasmids containing the PCR product inserts were transformed into competent E. coli strain INV-alpha F' (Invitrogen Corp.) for amplification. Plasmid DNA from these host cells was prepared using the standard alkaline lysis method (Sambrook et al., Supra), and the plasmid DNA was then electrophoresed through an approximately 1.5 percent agarose gel. A portion of the DNA was blotted on to Hybond-N membrane paper (Amersham, Oakville, Ontario, Canada) and hybridized with random-primed, $^{32}P$ labeled DNA fragments of murine IRF-1 and IRF-2 using the manufacturer's protocol (Amersham). Plasmid DNA from clones that did not hybridize with either IRF-1 or IRF-2 fragments was sequenced using the US Bioscience Sequenase kit (US Bioscience, Cleveland, Ohio). One clone, "Spl 5", contained a novel nucleotide sequence as determined from a search in Genbank. This clone was labeled with $^{32}P$ by random priming (Amersham procedure) and was then used to screen a mouse IL-4 induced spleen cDNA library (Clonetech, Palo Alto, Calif.). After hybridization, the filters containing the cDNA library clones were washed first with 1×SSC and 0.1 percent SDS for about 30 minutes at about 65° C. and then with 0.2×SSC and 0.1 percent SDS for about 30 minutes at about 65 ° C. Two LSIRF cDNA clones lacking the ATG start codon were obtained. One of these clones, "C13", was used to rescreen the same library, yielding an approximately 5 kb clone, "C16", which also lacked the 5' sequence. Clone C16 was then used to screen a λZAPII mouse spleen cDNA library (Stratagene, La Jolla, Calif.) and several partial clones having a putative ATG start codon were obtained. A complete cDNA sequence containing the entire coding LSIRF region was obtained by creating an artificial clone using PCR with a 5' extended primer. This clone was inserted into the vector pBSII to generate the plasmid PV-1, and the sequence of LSIRF was verified.

The predicted amino acid sequence was obtained for each of the partial cDNA clones, and some of the clones had an extra glutamine at amino acid position 164. The full-length cDNA sequence of PV-1, which is about 1.4 kb, is set forth in FIG. 1. The PV-1 cDNA contains the extra glutamine at amino acid position 164. A predicted full length amino acid sequence for LSIRF based on the LSIRF cDNA sequence is set forth in FIG. 2.

Example 2

Genomic Cloning of Mouse LSIRF

An approximately 630 bp portion of the C16 clone of the LSIRF cDNA was PCR amplified using the following primers:

CAGCCCGGGGTACTTGCCGCTGTC (SEQ ID NO:7)
AGACCTTATGCTTGGCTCAATGGG (SEQ ID NO:8)

PCR conditions were 94° C. for 1 minute and 72° C. for 30 seconds.

The PCR fragment obtained was purified by 1 percent agarose gel electrophoresis, followed by passage through a Spin-X column (CoStar Corp., Cambridge, Mass.). This fragment was then labeled with $^{32}P$ using the random primer technique (Amersham), and subsequently used to screen a genomic library prepared from kidney tissue of a 129/J mouse. Several clones were obtained by washing at 65° C. in 0.1×SSC and 0.1 percent SDS. Two of these clones (sizes 12 and 15 kb) were subcloned into the vector pBSII (Stratagene, La Jolla, Calif.) for sequencing. The clones contained overlapping sequence, permitting the identification of about 2 kb of 5' flanking sequence. The 5' flanking sequence is set forth in FIG. 3. A genomic sequence containing the exons and introns of a murine LSIRF gene is set forth in FIG. 4, and the inconsistencies in the sequence due to sequence uncertainty are indicated as "R" for A or G, "S" for G or C, "M" for A or C, and "K" for T or G. The ambiguities are:

M at nucleotides 748, 4159, 7413, and 10357;
R at nucleotides 5277, 5310, 10564, and 11713;
K at nucleotides 4513, 5885, and 9812;
S at nucleotide 6425.

All ambiguities are in the introns, thus not affecting the actual nucleotide sequence of the exons that comprise the coding region of LSIRF.

The nucleotide (cDNA and genomic) sequences and the deduced amino acid sequence of LSIRF were compared with all sequences in the GenBank and SwissProt databases, and no identical sequences were found. However, the amino terminus sequence of LSIRF had homology with other members of the IRF family. The highest homology was with the polypeptide ICSBP (interferon consensus sequence binding protein), which shares 83 percent homology (allowing for a one amino acid gap) with LSIRF at the amino terminus.

Example 3

Mouse LSIRF Expression

The LSIRF full length cDNA sequence was excised from the plasmid PV-1 by EcoRI restriction digest. The LSIRF gene was isolated from a 0.7% agarose gel after electrophoresis, blunt ended using Klenow DNA polymerase, and ligated into the NheI site of the plasmid pETL (BlueBacII, Invitrogen Company) to generate the plasmid pETL-LSIRF. The plasmid was amplified in *E. coli* cells strain DH5-alpha (grown in the presence of ampicillin) using standard culturing methods and conditions. Purified plasmid containing the LSIRF gene in the proper orientation (as determined by restriction endonuclease mapping with EcoRI, HindIII, or PvuII digestion) was co-transfected into Sf9 insect cells (available from the American Type Culture Collection, 12301 Parklawn Drive, Rockville, Md USA) together with linearized baculovirus genomic DNA (Invitrogen Corp., San Diego, Calif., USA), and the cells were incubated for about 48 hours at about 28° C. in Grace's medium supplemented with yeastolate, lactalbumin hydrolysate, and 10 percent fetal calf serum.

After incubation, the cells were harvested and plaque assays were performed (Richardson, ed., *Meth. Mol. Biol.*, vol 39: *Baculovirus Expression Protocols*, Humana Press, Totowa, N.J. [1995]) in the presence of Bluo-gal (Gibco-BRL, Grand Island, N.Y., USA) in order to isolate recombinant virus. Blue recombinant plaques were selected after 5–7 days of culturing and the plaques were amplified in 24 well microtiter plates containing Sf9 cells. Further amplification of recombinant virus was performed by large-scale cell culturing in tissue culture flasks until a titer of about $10^8$ pfu/ml was obtained. Expression of LSIRF was verified by infecting Sf9 cells at a multiplicity of infection of about 1 pfu/cell and harvesting cells at 0, 24, 48, 72, and 96 hours post-infection. Cell lysates were then prepared by solubilization in SDS-PAGE sample buffer (100 mM DTT, 80 mM Tris-HCl, pH 6.8, 10 percent glycerol, 0.0012 percent bromophenol blue) and were analyzed by Western blot analysis.

Protein extracts from both Sf9 cells and mouse peripheral lymphocytes were analyzed for the presence of LSIRF polypeptide. Lymphocytes were prepared from lymph nodes excised from mice by passing the lymph node tissue through a fine mesh screen. The lymphocytes were maintained in Iscove's medium supplemented with 10 percent fetal calf serum. Protein extracts from the Sf9 and lymphocyte cells were prepared using the manufacturer's protocol for Sf9 cells (Pharmingen, San Diego, Calif.) or methods set forth in Sambrook et al., (*Molecular Cloning: A Laboratory Manual*, Cold Spring Harbor Laboratory Press, Cold Spring Harbor, N.Y. [1989]; for lymphocyte cells). The proteins were resolved on an 8 percent polyacrylamide/0.1 percent SDS gel and the gel was transferred to Immobilon-P membrane (millipore Company) using standard procedures. The blot was first incubated with blocking buffer (4 percent skim milk and 0.05 percent Tween-20 in 1×PBS) for 1 hour at room temperature. LSIRF rabbit polyclonal antisera raised against a LSIRF carboxy-terminus peptide was then added to the blot at dilution of about 1:2000 (in a solution of 1 part blocking buffer to 1 part PBS). The LSIRF peptide injected into the rabbit to generate antibody was:

GYELPHEVTTPDYHR (SEQ ID NO.:9)

After incubation with LSIRF antibody for about 1 hour, the blot was washed and the LSIRF antibody was detected with goat anti-rabbit horseradish peroxidase-conjugated antibody at a dilution of about 1:5000.

The results indicate that an approximately 51 kD band (the predicted molecular weight of LSIRF) was recognized by anti LSIRF antibody for both peripheral T cells stimulated with anti-CD3 antibodies and recombinant Sf9 cells.

Example 4

Mouse LSIRF Expression Analysis

A. Tissue Blots

To assess the tissue specificity of LSIRF transcripts, total RNA was prepared from mouse brain, lung, thymus, bone marrow, spleen, liver, intestine, pancreas, salivary gland, testis, heart and smooth muscle tissue using methods described by Wangm et al. (*EMBO J.*, 10:2437–2450 [1991]). The RNAs were electrophoresed through a 1 percent agarose/formaldehyde gel using standard procedures and then transferred to nitrocellulose paper as described in Sambrook et al., supra. The blots were then hybridized with a random-primed $^{32}$P labeled 1.4 kb cDNA containing the entire coding region of LSIRF (the insert from PV-1) and subsequently washed as described by Stewart et al. (*Meth. Mol. Cell Biol.*, 1:73–76 [1989]) at about 50° C. in 0.2×SSC and 0.1 percent SDS.

The results as shown in FIG. 5 indicate that a LSIRF transcript of about 5.5 kb is present largely in spleen and bone marrow tissue with weaker transcripts of the same size in thymus and lung tissues. Surprisingly, no additional bands were observed. In addition, FIG. 6 indicates that lymph node tissue also contains LSIRF transcripts.

Various T cell lines including CTLL-2, D10.G4.1, HT-2, EL-4, and BW5147 (all cells available from the American Type Culture Collection, 12301 Parklawn Drive, Rockville, Md., USA) were evaluated for LSIRF expression using Northern blot analysis. RNA was extracted from these cell lines using the method of Chomczynski et al. (Anal. Biochem., 162:156–159 [1987]). The cell lines were maintained at 37° C. and 5 percent $CO_2$ in Iscove's medium supplemented with 10 percent fetal calf serum and 2 mM L-glutamine. The first three cell lines are believed to be peripheral T cell lineages, while the last two are believed to be immature T cell lineages. Cultures of HT-2 and CTLL-2 cells were supplemented with 50 U/ml of IL-2 (Genzyme Inc., Cambridge, Mass) and 50 $\mu$M 2-mercaptoethanol; cultures of D10.G4.1 were supplemented with 50 U/ml of IL-1 (Genzyme Inc., Cambridge, Mass.), 50 U/ml of IL-2, and 50 mM 2-mercaptoethanol.

Northern blots were prepared from total RNA, transferred to Hybond N paper, and probed with the 1.4 kb random primed cDNA as described above using the Stewart et al., supra methods.

The results indicate that LSIRF transcripts are visible only in the peripheral T cell lines, suggesting that LSIRF is preferentially expressed in mature T cells. Similar analyses of mRNA transcripts in the pre-B cell line CB17.51, the B cell line WEHI231 (American Type Culture Collection), and plasmacytoma cell line J558 (American Type Culture Collection) show the presence of the transcript in all cell lines, with J558 having the strongest signal.

The induction of LSIRF in primary lymphocytes obtained from spleen or lymph nodes was evaluated by adding various stimulators to the cultured cells and assessing the LSIRF mRNA levels. The stimulants used for lymph node cells were 1000 U/ml murine interferon-beta (IFN-beta; Lee Biomolecular Research, San Diego, Calif.), 100 U/ml murine interferon-gamma (IFN-gamma; Genzyme Inc., Cambridge, Mass.), or 10 ng/ml murine tumor necrosis factor (TNF; Genzyme Inc.). Splenocyte cells were treated with 20 $\mu$g/ml anti-IgM antibodies, 10 $\mu$g/ml lipopolysaccharide (LPS; a bacterial endotoxin), 10 ng/ml PMA (phorbol myristate acetate; Sigma Chemical Co., St. Louis, Mo.), 1 mg/ml cyclosporin A (CsA; Sandoz Company, Basel, Switzerland), 10 $\mu$g/ml of Concanavalin A (ConA; Sigma), or 1 or 10 $\mu$g/ml cycloheximide (CHX; Sigma). All cells were treated for 6 hours at 37° C.

Figure 6:
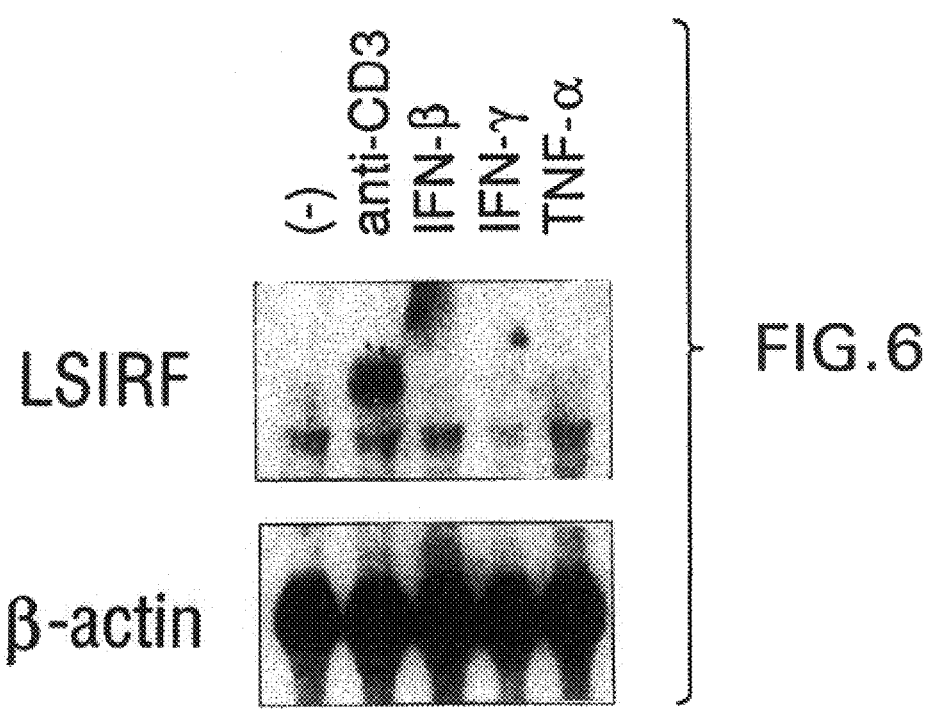
FIG. 6 depicts a Northern blot of RNA from mouse lymphocytes treated without stimulators (–), or with the stimulators as indicated. The blot was probed with a radio-labeled LSIRF probe to identify those stimulators that induce LSIRF transcription. The same blot, probed with a radiolabeled beta actin probe, is also shown.
Figure 7:
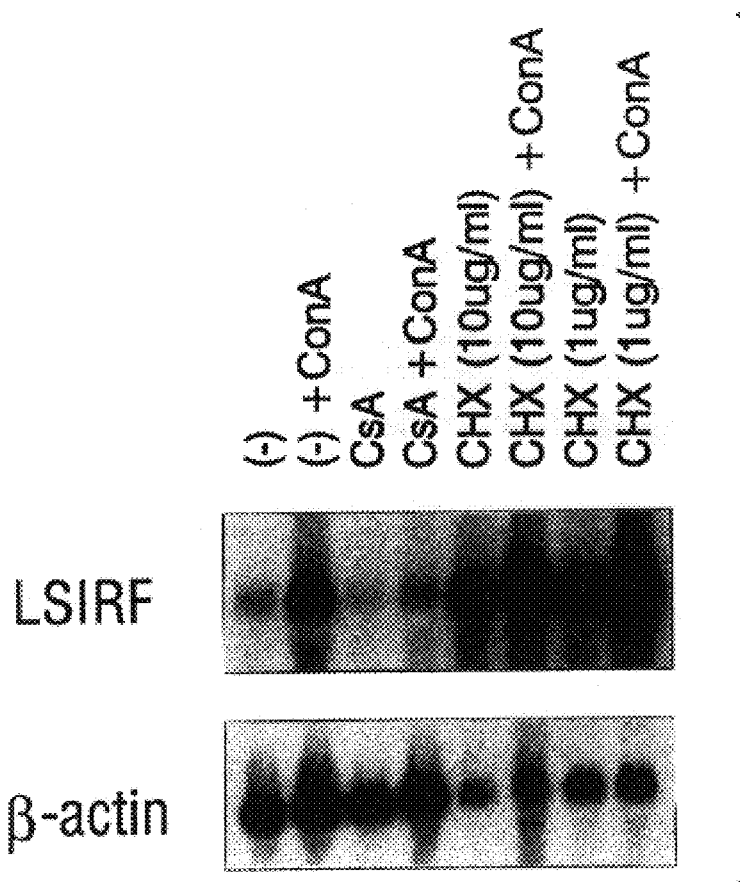
FIG. 7 depicts a Northern blot of mouse splenocytes treated without a stimulator (–) or with one or more stimulators as indicated, and then probed with a radiolabeled LSIRF probe. The same Northern blot probed with a radio-labeled beta-actin probe is also shown.
Figure 8:
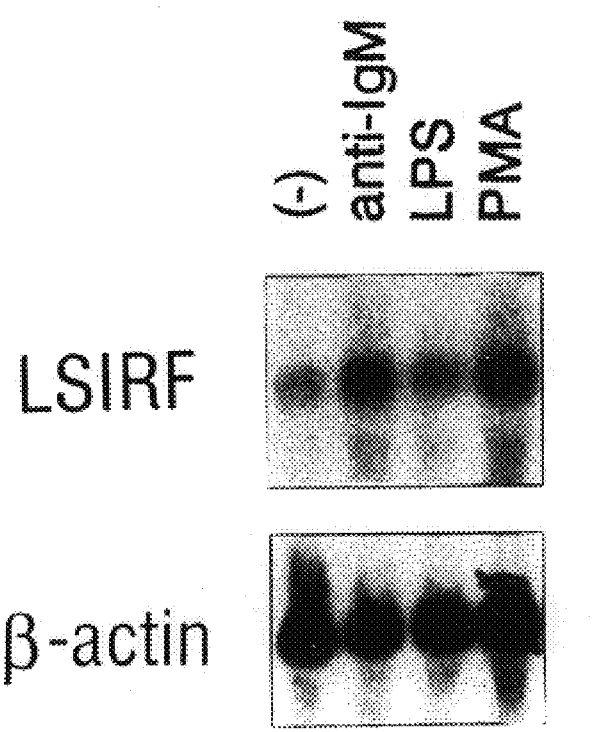
FIG. 8 depicts a Northern blot of mouse splenocytes treated without a stimulator (–) or with a stimulator as indicated, and then probed with a radiolabeled LSIRF probe. The same Northern blot probed with a radiolabeled beta-actin probe is also shown.

The results are shown in FIGS. 6, 7, and 8. In all Figures, beta actin is shown as an indicator of the quantity of total RNA analyzed.

FIG. 6 shows that anti-CD3 antibodies did induce LSIRF transcription. Most surprisingly however, the interferons did not induce LSIRF transcripts. This is in stark contrast to other known IRFs, as transcripts of both of other known IRFs are induced by interferons.

FIG. 7 shows that cycloheximide, a protein synthesis inhibitor, induces LSIRF transcription. This result was not expected, since cycloheximide does not induce transcription of the IRF-1 or IRF-2 genes.

FIG. 8 shows that anti-IgM and PMA induce LSIRF transcripts. Such induction by anti-IgM was surprising, as it indicates that LSIRF is expressed in B cells as well as in T cells.

B. Gel Shift Assay

An electrophoretic mobility shift assay was conducted to assess whether the LSIRF polypeptide is a DNA binding protein. Nuclear extracts from control Sf9 cells (transfected with wild type baculovirus only) and LSIRF expressing Sf9 (transfected with baculovirus containing the LSIRF cDNA) cells were prepared as follows. The Sf9 cells were pelleted and were then washed twice in PBS. After the final wash, the cells were resuspended in 0.5 ml of "H-buffer" (hypotonic buffer) per 10⁷ cells (H-buffer consists of: 25 mM Hepes-NaOH, pH 8.0, 10 mM KCl, 5 mM $M_gCl_2$, 0.5 mM EDTA, and 0.5 mM DTT) and were incubated on ice for about 30 min during which time the cells swelled due to the hypotonic buffer. The cells were then disrupted with 15 strokes of a type B pestle in a dounce homogenizer. The nuclei were isolated from the cell debris by pelleting at about 4° C. in a microfuge at 10 K rpm for about 10 min. The pellets, which contained the majority of nuclei, were then extracted by resuspending in 0.5 ml of N-buffer per 10⁷ cells (N-buffer consists of: 25 mM Hepes-NaOH pH 8.0, 400 mM KCl, 5 mM $M_gCl_2$, 0.5 mM EDTA, 10 percent glycerol, and 0.5 mM DTT) and incubating on ice for about 20 minutes. The suspension was then centrifuged at 4° C. in a microfuge at 15K rpm for about 15 minutes. The supernatant, which contained the majority of LSIRF polypeptide, was buffer exchanged to remove excess salt using a Centricon 10 microconcentrator (Amicon Corporation). The diluting buffer for concentration was E-buffer (25 mM Hepes-NaOH, pH 8.0, 50 mM KCl, 5 mM $M_gCl_2$, 0.5 mM EDTA, 15 percent glycerol, and 0.5 mM DTT). H-buffer, N-buffer, and E-buffer all contained the following protease inhibitors: 0.5 mM PMSF, 0.5 μg/ml leupeptin, and 0.5 μg/ml aprotinin).

To assess electrophoretic mobility of a particular DNA fragment due to LSIRF binding of the fragment,the extracts were incubated with a double stranded ³²P-labeled DNA probe. The sequence of the sense strand of this probe, a wild-type murine MHC IRSE binding sequence, is set forth below:

TGCAGAAGTGAAACTGAGG (SEQ ID NO: 10)

For the binding reaction, about 25×10³ cpm (corresponding to about 1×10⁻¹¹ moles of the probe) was prepared in binding reaction buffer (12 mM Hepes-KOH, pH 7.9, 30 mM KCl, 60 μM EGTA, 0.3 mM DTT, 2.5 percent Ficoll, 0.6 μg poly(dI-dC) [obtained from Pharmacia], and 0.05 percent NP-40). The nuclear extracts were prepared by diluting approximately 8-fold in E-buffer containing about 0.1 mg/ml of BSA (bovine serum albumin) to a final concentration of about 14 μg total protein/ml for the LSIRF containing reactions, and about 22 μg/ml for the control reactions. The binding reaction was started by adding about 1 μl of the nuclear extract to about 6.24 μl of probe solution, which, in some cases, also contained unlabeled "competitor" DNA fragments. The sequence of each of these fragments is set forth below in Table 1. The competitor fragments were added at an approximately 750 fold molar excess (as compared to the labeled fragment). The nuclear extract/probe solution was incubated at about 23° C. for about 20 minutes and was then loaded on to a 9 percent polyacrylamide gel (prepared with 0.25×TBE) that had been pre-run at about 250 volts for about 2 hours before sample application. The gel was run for about two hours at about 300 volts to separate protein-DNA complexes from the unbound DNA probe. The gel was then dried and exposed to film to assess DNA probe migration shift due to protein binding.

TABLE 1

| FRAGMENT | SEQUENCE | |
|---|---|---|
| mMHC ISRE wt | TGCAGAAGTGAAACTGAG | (SEQ ID NO:11) |
| mISRE mt1 | TGCAGAAGTGAAACCTGG | (SEQ ID NO:12) |
| mISRE mt2 | TGCAGAAGTGAACATGAG | (SEQ ID NO:13) |
| mISRE mt3 | TGCAGAAGTGGTCCTGAG | (SEQ ID NO:14) |
| mISRE mt4 | GCTAGAAGTGAAACTGAG | (SEQ ID NO:15) |
| mIgλ B | AAAGGAAGTGAAACCAAG | (SEQ ID NO:16) |
| mIgkappa E3' | TGAGGAACTGAAAACAGA | (SEQ ID NO:17) |
| hISG54 ISRE | GGGAAAGTGAAACTAG | (SEQ ID NO:18) |

In Table 1, "m" indicates mouse sequence, and "h" indicates human sequence.

Figure 9:
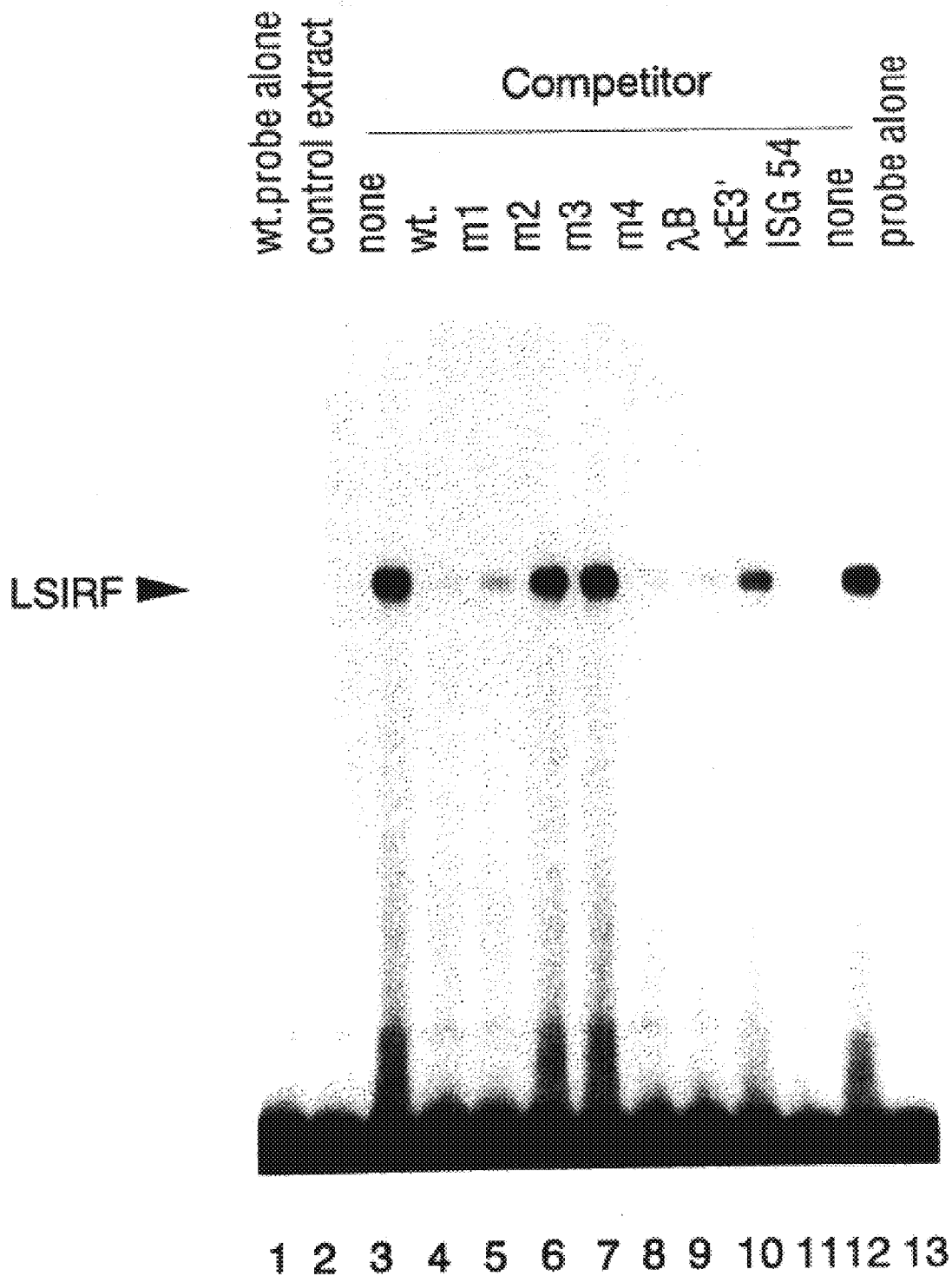
FIG. 9 depicts a gel shift binding assay of LSIRF binding of the mouse MHC ISRE. Nuclear extracts from control baculovirus infected SF9 insect cells (lane 2) or from SF9 cells infected with baculovirus containing the LSIRF gene (lanes 3–12) were incubated with a both a radiolabeled mouse MHC ISRE probe and an indicated competitor DNA fragment (the sequence of the competitor fragments is set forth in Table 1). Lanes 1 and 13 contain radiolabeled MHC ISRE probe alone.

The results are shown in FIG. 9. As can be seen, the wild type MHC ISRE sequence binds LSIRF protein. In addition, two ISRE DNA fragment mutants, m1 and m4, compete well for binding as do two other DNA fragments, Ig lambda B and ISG54.

Example 5

Human LSIRF Cloning

To identify the human cDNA encoding LSIRF, a human lymphocyte cDNA library (Clontech, Palo Alto, Calif.; catalog number HL 1031a) was screened using the mouse PV-1 clone. Screening conditions were overnight at 65° C. in Church buffer (Church and Gilbert, *Proc. Natl. Acad. Sci. USA*, 81:1991–1995 [1984]). The filters were washed twice for about 30 minutes each in 2×SSC and 0.1 percent SDS. Of about one million plaques screened, two positive clones were identified, isolated, and the DNA was purified using standard techniques. The clones were subcloned into the EcoRI site of pBluescript (Stratagene, Lajolla, Calif.). The longest of these clones, termed H14, which was greater than about 2 kb, was sequenced. The seqeunce indicated that this clone was a hybrid of the TNF (tumor necrosis factor) receptor p55 (about 400 base pairs) and about 1 kb of sequence that was highly homologous to exons 3–9 of mouse LSIRF sequence. In addition, this clone had a conserved stop codon, a splice donor sequence, and about 600 base pairs of intron 9. It was thus concluded that this 1019 base pair seqeuence represented a portion of human LSIRF sequence. This 1019 base pair sequence was amplified by PCR using the following primers:

CTGGACATCTCAGACCCGTACAAAGTG (SEQ ID NO: 19)

CTTGACATTTTTCATTCTTGAATAGAG (SEQ ID NO: 20)

Amplification conditions were 94° C. for 30 seconds, 65° C. for 30 seconds, and 72C. for about 90 seconds. About 500 ng of H14 template was used in the presence of Taq polymerase, and about 15 cycles of PCR were conducted.

The resulting PCR product was ligated directly into the TA cloning kit vector PCRII (Invitrogen, San Diego, Calif.) and sequenced to verify that the proper fragment had been amplified. This 1019 base pair cDNA fragment, termed "FISH", was then used to screen a human leukocyte 5'-stretch cDNA library (Clontech; catalog number HL 1169x). The screening conditions were: about 65° C. overnight in Church buffer, followed by rinsing twice for about 30 minutes in 2×SSC and 0.1 percent SDS, and then twice in 0.2×SSC and 0.1 percent SDS for about 30 minutes. One plaque of about 500,000 was identified, and the DNA purified and sequenced. This clone, termed HIRF4λDR2, contained intron 2 and full length exon 3 (only a portion of exon 3 was found in the H14 clone), as well as exons 5, 7, 8 and intron 8. Exons 4 and 6 were presumably spliced out or missing.

To obtain the remainder of the LSIRF coding sequence, two approaches were employed. First, a human placental genomic library in the vector lambda fix 2 (Stratagene, LaJolla, Calif.) was screened using the FISH cDNA as a probe. Screening conditions were about 65° C. overnight in Church buffer, followed by rinsing twice for about 30 minutes in 2×SSC and 0.1 percent SDS, and then twice in 0.2×SSC and 0.1 percent SDS for about 30 minutes. Ten phage clones were isolated, and the DNA was purified from one clone, termed HG-1. This DNA was digested with restriction endonucleases Bam HI, Sac I, and xba I and the fragments were subcloned into the cloning vector pMOB (Strathmann et al., *Proc. Natl. Acad. Sci. USA*, 88:1247–1250 [1991]). The sequence of each fragment was obtained and compared with the mouse LSIRF sequence. The promoter, exon I, and exon II of human LSIRF were identified in this clone based on homology to the mouse sequence.

The second approach used was a RACE reaction using the Clontech Marathon® kit and following the manufacturer's protocol. A B-cell lymphoma line called OCILY8 (see Blood, 69:1307–1314 [1987]) which had been shown by previous Northern blot analysis to have high LSIRF expression was used. The resulting RACE product was sequenced and was found to match the genomic sequence of exons one and two (obtained as described above).

To produce an open reading frame the FISH cDNA was excised from the EcoRI site of the vector PCRII and ligated into the EcoRI site of PGEX4T3 (Promega, Madison, Wis.) to form the vector pGEX4T3-FISH. To obtain the 5' end of the open reading frame in a form that would permit it to be fused to the FISH clone, human spleen Marathon® (Clontech, catalog no. 7412-1) ready cDNA was used with the following two primers for amplification:

TGCCCTCAGCTCCGAGTCCAG (SEQ. ID. NO.: 21)

AACCATTTTCACAAGCTG (SEQ. ID. NO.: 22)

Amplification was accomplished using PCR under the following conditions: 94° C. for 30 seconds, 64° C. for 30 seconds, and 68° C. for one minute. Thirty cycles were performed using Expand High Fidelity Polymerase (Boehringer Manheim). Using this procedure, the sequence of the N-terminus of the LSIRF was amplified giving an expected DNA fragment size of approximately 600 base pairs.

The approximately 600 base pair fragment was re amplified by PCR using SEQ. ID. NO.: 22 (set forth above) and SEQ ID NO.: 23 as set forth below:

G G AT C C G G AT C C AT G A A C T G G A G G G C G-GCGGCCGAGGC (SEQ. ID. NO: 23)

Fifteen cycles of PCR were conducted as follows: 94° C. for 30 seconds, 64° C. for 30 seconds, and 72° C. for 90 seconds using native PFU polymerase (Stratagene, LaJolla, Calif.).

The PGEX4T3 vector containing the FISH insert (pGEX4T3-FISH) was digested with both BamHI and Sac II, thereby removing the 5' portion of the FISH insert. The approximately 600 base pair PCR product from above was digested with the same enzymes and ligated into the pGEX4T3-FISH vector to form the full length open reading frame construct pGEX4T3 LSIRF Bam HI/EcoRI, the coding region of which is set forth in FIG. 10. The predicted amino acid sequence is set forth in FIG. 11. This clone was evaluated by production of a GST fusion protein (Pharmacia) following the manufacturer's protocol. The predicted size of the fusion protein was about 79 kD, of which about 27 kD is GST protein, and about 52 kD is LSIRF protein. The fusion protein migrated on 8 percent SDS-PAGE to the expected size of about 79 kD as determined by Coomassie blue staining.

Northern blot analysis of human LSIRF indicated that this gene is expressed primarily in spleen tissue and peripheral blood tissue, with a lower level seen in colon and intestinal tissue. In addition, using a multiple cancer cell line Northern blot obtained from Clontech (catalog no. 7757-1), weak expression of the gene was seen in the human B cell Burkitt's lymphoma line Raji, and strong expression was observed in the human melanoma line G361 cancer line.

Based on DNA sequencing of several clones containing partial hLSIRF sequence, it is thought that two forms of the hLSIRF sequence exist. One form, the "Single Q" form, contains the "CAG" codon at bases 490–492, which codes for amino acid Q (Gln) at amino acid position 164. A second form of LSIRF DNA, the "Double Q" form, contains an additional "CAG" codon between bases 492 and 493 of the "Single Q" form, resulting in an additional amino acid Q (Gln) between amino acids 163 and 164 of the "Single Q" form. Aside from this one difference, the amino acid and nucleic acid sequences of the two forms are identical.

The full length "Single Q" DNA sequence encoding human LSIRF (hLSIRF) in the vector pGEX4T3 was deposited with the ATCC as accession number 98016 on Mar. 27, 1996. In addition, the full length human LSIRF sequence encoding the "Double Q" form of the hLSIRF protein was deposited with the ATCC on Mar. 27, 1996 as accession number 98017.

We claim:

1. An isolated polypeptide or fragment thereof having the specific DNA binding activity of a LSIRF polypeptide, wherein the polypeptide has the amino acid sequence of SEQ ID NO:2, or SEQ ID NO:25.

2. A polypeptide having the amino acid sequence of SEQ ID NO: 2.

3. A polypeptide of claim 1 that is the product of a prokaryotic or eukaryotic host cell expression of an exogenous nucleic acid molecule sequence, wherein the polypeptide has the amino acid sequence of SEQ ID NO:2, or SEQ ID NO:25.

4. A biologically active LSIRF polypeptide having an amino acid sequence encoded by a nucleic acid molecule selected from the group consisting of:

a) a nucleic acid molecule having a nucleotide sequence of SEQ. ID. NO: 1;
   b) a nucleic acid molecule having a nucleotide sequence of SEQ. ID. NO: 4;
   c) a nucleic acid molecule having a nucleotide sequence of SEQ. ID. NO: 24 or the "Double Q" variant thereof;
   d) a nucleic acid molecule having a nucleotide sequence encoding the amino acid sequence of SEQ. ID. NO: 2;
   e) a nucleic acid molecule having a nucleotide sequence encoding the amino acid sequence of SEQ. ID. NO: 25 or the "Double Q" variant thereof; and
   f) a nucleic acid molecule having a nucleotide sequence which hybridizes under washing conditions of 0.015 M NaCl, 0.005 M NaCitrate, and 0.1 percent SDS at 55–65° C. with the complement of a nucleic acid molecule of any of (a), (b), (c), (d), or (e), or with the complement of a fragment thereof.

5. A polypeptide having the amino acid sequence of SEQ ID NO: 25, or the "Double Q" variant thereof.

6. A polypeptide of claim 4 that is the product of a prokaryotic or eukaryotic host cell expression of an exogenous nucleic acid molecule sequence.

* * * * *

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
    (A) LENGTH: 1353 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:1:

```
ATGAACTTGG AGACGGGCAG CCGGGGCTCA GAGTTCGGCA TGAGCGCAGT GAGCTGCGGC    60
AATGGGAAAC TCCGACAGTG GTTGATCGAC CAGATCGACA GCGGCAAGTA CCCCGGGCTG   120
GTGTGGGAGA ACGAGGAGAA GAGCGTCTTC CGCATCCCGT GGAAACACGC GGGCAAGCAG   180
GACTACAATC GTGAGGAGGA CGCTGCCCTC TTCAAGGCTT GGGCATTGTT TAAAGGCAAG   240
TTCCGAGAAG GGATCGACAA GCCAGATCCT CCTACTTGGA AGACAAGATT ACGATGTGCT   300
CTGAACAAGA GCAATGACTT TGAGGAATTG GTCGAGAGGA GCCAGCTGGA TATCTCTGAC   360
CCATACAAGG TGTACAGGAT TGTTCCAGAG GGAGCCAAAA AAGGAGCAAA GCAGCTCACT   420
TTGGATGACA CACAGATGGC CATGGGCCAC CCCTACCCCA TGACAGCACC TTATGGCTCT   480
CTGCCAGCCC AGCAGGTTCA TAACTACATG ATGCCACCCC ATGACAGGAG CTGGAGGGAT   540
TATGCCCCTG ACCAGTCACA CCCAGAAATC CCATATCAAT GTCCTGTGAC GTTTGGCCCA   600
CGAGGCCACC ACTGGCAAGG CCCATCTTGT GAAAATGGTT GCCAGGTGAC AGGAACCTTT   660
TATGCTTGTG CCCCACCTGA GTCCCAGGCT CCTGGAATCC CCATTGAGCC AAGCATAAGG   720
TCTGCTGAAG CCTTGGCGCT CTCAGACTGC CGGCTGCATA TCTGCCTGTA TTACCGGGAC   780
ATCCTCGTGA AAGAGCTGAC CACGACGAGC CCTGAAGGCT GCCGGATCTC CCACGGACAC   840
ACCTATGATG TTAGCAACCT GGACCAGGTC CTGTTTCCCT ACCCGGACGA CAATGGACAG   900
AGGAAGAACA TTGAGAAGTT GCTGAGCCAC CTGGAGAGGG GACTGGTCCT CTGGATGGCT   960
CCAGATGGGC TTTATGCCAA AAGACTCTGC CAGAGTAGGA TCTACTGGGA TGGGCCCCTG  1020
GCACTGTGCA GCGATCGGCC CAACAAGCTA GAAAGAGACC AGACTTGCAA GCTCTTTGAC  1080
ACACAGCAGT TTCTATCAGA GCTGCAAGTG TTTGCTCACC ATGGCCGGCC AGCACCGAGA  1140
TTCCAGGTGA CTCTGTGCTT TGGTGAGGAG TTTCCAGACC CTCAGAGACA GAGGAAGCTC  1200
ATCACAGCTC ATGTGGAACC TCTGCTAGCC AGACAACTGT ATTACTTTGC TCAACAAAAC  1260
ACTGGACATT TCCTGAGGGG CTACGAGTTA CCTGAACACG TTACCACTCC AGATTACCAC  1320
CGCTCCCTCC GTCATTCTTC CATCCAAGAG TGA                               1353
```

(2) INFORMATION FOR SEQ ID NO:2:

(i) SEQUENCE CHARACTERISTICS:
        (A) LENGTH: 450 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Asn Leu Glu Thr Gly Ser Arg Gly Ser Glu Phe Gly Met Ser Ala
1               5                   10                  15

Val Ser Cys Gly Asn Gly Lys Leu Arg Gln Trp Leu Ile Asp Gln Ile
            20                  25                  30

Asp Ser Gly Lys Tyr Pro Gly Leu Val Trp Glu Asn Glu Glu Lys Ser
        35                  40                  45
```

```
Val Phe Arg Ile Pro Trp Lys His Ala Gly Lys Gln Asp Tyr Asn Arg
     50                  55                  60
Glu Glu Asp Ala Ala Leu Phe Lys Ala Trp Ala Leu Phe Lys Gly Lys
 65                  70                  75                  80
Phe Arg Glu Gly Ile Asp Lys Pro Asp Pro Thr Trp Lys Thr Arg
                     85                  90                  95
Leu Arg Cys Ala Leu Asn Lys Ser Asn Asp Phe Glu Glu Leu Val Glu
                100                 105                 110
Arg Ser Gln Leu Asp Ile Ser Asp Pro Tyr Lys Val Tyr Arg Ile Val
                115                 120                 125
Pro Glu Gly Ala Lys Lys Gly Ala Lys Gln Leu Thr Leu Asp Asp Thr
            130                 135                 140
Gln Met Ala Met Gly His Pro Tyr Pro Met Thr Ala Pro Tyr Gly Ser
145                 150                 155                 160
Leu Pro Ala Gln Gln Val His Asn Tyr Met Met Pro Pro His Asp Arg
                165                 170                 175
Ser Trp Arg Asp Tyr Ala Pro Asp Gln Ser His Pro Glu Ile Pro Tyr
                180                 185                 190
Gln Cys Pro Val Thr Phe Gly Pro Arg Gly His His Trp Gln Gly Pro
                195                 200                 205
Ser Cys Glu Asn Gly Cys Gln Val Thr Gly Thr Phe Tyr Ala Cys Ala
                210                 215                 220
Pro Pro Glu Ser Gln Ala Pro Gly Ile Pro Ile Glu Pro Ser Ile Arg
225                 230                 235                 240
Ser Ala Glu Ala Leu Ala Leu Ser Asp Cys Arg Leu His Ile Cys Leu
                245                 250                 255
Tyr Tyr Arg Asp Ile Leu Val Lys Glu Leu Thr Thr Thr Ser Pro Glu
                260                 265                 270
Gly Cys Arg Ile Ser His Gly His Thr Tyr Asp Val Ser Asn Leu Asp
                275                 280                 285
Gln Val Leu Phe Pro Tyr Pro Asp Asp Asn Gly Gln Arg Lys Asn Ile
            290                 295                 300
Glu Lys Leu Leu Ser His Leu Glu Arg Gly Leu Val Leu Trp Met Ala
305                 310                 315                 320
Pro Asp Gly Leu Tyr Ala Lys Arg Leu Cys Gln Ser Arg Ile Tyr Trp
                325                 330                 335
Asp Gly Pro Leu Ala Leu Cys Ser Asp Arg Pro Asn Lys Leu Glu Arg
                340                 345                 350
Asp Gln Thr Cys Lys Leu Phe Asp Thr Gln Gln Phe Leu Ser Glu Leu
                355                 360                 365
Gln Val Phe Ala His His Gly Arg Pro Ala Pro Arg Phe Gln Val Thr
            370                 375                 380
Leu Cys Phe Gly Glu Glu Phe Pro Asp Pro Gln Arg Gln Arg Lys Leu
385                 390                 395                 400
Ile Thr Ala His Val Glu Pro Leu Leu Ala Arg Gln Leu Tyr Tyr Phe
                405                 410                 415
Ala Gln Gln Asn Thr Gly His Phe Leu Arg Gly Tyr Glu Leu Pro Glu
                420                 425                 430
His Val Thr Thr Pro Asp Tyr His Arg Ser Leu Arg His Ser Ser Ile
            435                 440                 445
Gln Glu
    450
```

(2) INFORMATION FOR SEQ ID NO:3:

(i) SEQUENCE CHARACTERISTICS:
        (A) LENGTH: 2139 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
AAGGGGCCAC CTGGCCATTC CTTCCTCTCC ACCAGCAACA ATGGGAGCAT GTGATTCACA      60
AGGGAATCAC ATTCAACTAA AAAGAGAAAC CGGGGTATGC TGTTTGCAAG GAACGGTTGA     120
AACTGGAACT CAATATGTCG TGTGGTGTGA AATAAACGTG TGTCTCACAT GTTTTCCCAT     180
GCTGGGGGCA GGGGTAAGAA AGTAAAAGGC AGACTGGTTA AAGACATGGG GTGGGGAGGG     240
CTGGAGGGAC GAGTGGTAAG AAATGGCGAC AGAGGAGATG AAGGTAATGT CATAATGAAA     300
CCCATCACTG CTGTGTGCAA CTAATAGATG CTAATAAAAT AGGAAGTTTT AATGATTTAG     360
GTAGCTTATT GCTTGCATTC ACCTCACTGT TAAACTATCA CTTCTGGGGG ATCCACACAA     420
CGAGCGAGCG AGTAAACCAG AAGATGGCGT TGGAAGATTA GTAATCATAT CTTTTAAACA     480
AGATAACCAT GTGAAGTCTC AAAAGGTTTC TTGTAATGAC TGTTGTTTAA ACTTCTGAAA     540
ACAGAGGATG TAGATTGGCT GAGGAAAATG TTGAAACCGC CTAAGTCAAG GTAGAAGACA     600
CGTGTGTCTA AGTGAAAAAA AGAAAAAAGA AAAAAAAAAA AACCAAAAAC CTCGGGTTGG     660
CTGCTTCTGT CCTTAGTCTG TGCACGCTTT GAAGAAATGT AATTCCTCAG CAGCAAGGCT     720
GTGCTATCTG AAGCTACAAT CTCTGCTTTG CTCCGAGGTG TGTCTCTGGT GACCGGGATA     780
GTTCCCGACA GACAGAAGGT GTTCAAAGAA TATTTTTGAA TGAATGAAAC CCCAAAGGAA     840
GAAGAGGGGA AAATGGGTGT GACCAAAATT TTCTTTGAAC GAAACTCTGT TGTTTACTAC     900
CAGGGCTCTG ACAATGAAAA ACTAATTGGG GTGAAAGAAC GACATGGCAT CCTGTTAATT     960
TCTGAGAAAG CCTGTTGATG TTAGGAAAAA AAAACATGCC GGTGGGCATC TCTGCACCAG    1020
TTTTCCTGTG GCCAAAATCA GATGTTTCTC CTAAAGTCCA GAACCCAGGA TGGAAGATTA    1080
AAAGAAAAAC TGAGAAACAT GTGAAATGAA AAAGTTGTCA AAAGCTTTAC AAACGCTCCA    1140
AGTTGACCTG TGGTGGTGGT AATCTAAAAT GATACAGAAA CTGGTAGTCT GCTTGCTTAC    1200
CTGAAAACAC CAAGATAACA TATAAGCTCC AGGCATCCAA GCTGAGCTGG AGAAAGTCAG    1260
CGGCAAAAGC TCATGGAGTT TACATATGAA GGTCAAAGAA AACACGAAAA TAAAGTAAAA    1320
CCTTCAGTCA GCCTAGCTGT TCTATTTGGG GCATTGGTAC CTCACCGCCA ACTGCCTCCC    1380
ACGAGGCTGA GGTTAAAATT ATCATTTTAA GGTGAATTGA CATCCGGAAG CGCGCTAACT    1440
ACCTGAGTAC TCAGGGATCC CCCATCTCTT TTATGTTGCC ATGATTGAAA CTTTGGGGAC    1500
TGTGCTTGTC TGAGTCATCT CAATTCGTCG GTTTCATTCA CCCAACATGT ATAAGCGTTT    1560
CAAACACAGT ATTTGGGCCA CGGCTTATAA ACTTGCCTTT CTATTTTTCT TTTTAGTGAG    1620
CGTGATATTC TCTAAACGCT CAGAGAGACA AGACTCCGCT TGTTCAGGA  TGCTCCCGAC    1680
CTCTCTCAGT CTATCTCTTC TGTTACATCT GTGAGAACAA GTTCCCTGTG CTCCAGACTC    1740
TCCATCACTT CCCACCTGTC GATGAGCAGT TAGTAGTTAT CAGCTATGCT CAGTGCAGAT    1800
TCCAGTATCC CCTTTGTATG CCTCCACCTT CCACAGGAGG GGGGCCATAC CGACTTGTCC    1860
CATCCGGTTG AGGATTTCTG AGTACATCAG AGTCCCCAGC CCCCTCCACA GGAGGAGCTG    1920
AAGAAAGCCA GGGTTTGTCT GAAGTGGGAC AGCCCTTGAC CCGGTGGGCT CTAGTCCGAA    1980
GCTCCTGTTC CTGCGGGACA CCCAGGCACA AGGCAGAGGT GGGGGGCGGT CCTGGGTATG    2040
```

| GCCAACCCAC GCCCTCTCAA GGCGGGGCCG AAGCGCCCGC CCTGCACTCC GCCTCCGGCT | 2100 |
| CTATAAAGTT CCTCTTTCTC ACCTCACTTT CCTAGTTTC | 2139 |

(2) INFORMATION FOR SEQ ID NO:4:

(i) SEQUENCE CHARACTERISTICS:
        (A) LENGTH: 12537 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

| ACCACTTGAA CTTGGGACCC TTTGCTGCCC TCAGCTAAGA GTGCGGGTGA GGTAAGGCCT | 60 |
| GTAGTCGGGC AGAAGGAGGA GTGTGAGGCT GGTGGCAGAG GAAGCCTGGC TTCCATCTCT | 120 |
| GAGCCTGAGG GAGAATGCTG AGATAGCGGA CCCAGGCTCC GCTCATCTAC GCTGCCCTAG | 180 |
| GACCTGTGCA CTTCGGGTTT TGTATGAAGC TGTTTGGGTG GGAGTTCCAG AACATCCCCC | 240 |
| ACGGGCTGGG CGGGACGAGC TAATGGGACT GTGGTGTCAT CAAAGGATCG CACTGGCCAC | 300 |
| AGCTTGTCCT CAGAGGGACA GCCTCTGACT CTCTCTGCTC CAGTGGAAAG CTCCTTTCCA | 360 |
| GCCCTGGTTC CTAAAGGACC CAAACTCATC TAGGGCTCCA GAGCGTGATT CCTAGGCCGG | 420 |
| GCAGCCAAGA AGAGCTGAGA GCTCCAAACT TAGGGTGCTC AGAGCCCCTT TCCCCGCATG | 480 |
| CCCCTTCTTC ACTTCTCTGG CAAGAGTGCT AGTGTTGCTG TCCGCAGCAC CCCTTATTCC | 540 |
| CAGCCTCGGC TTCATTCCTG CCAGGGTTCG CGCTGACATT CTGCAGGTTG GAATCTCCTG | 600 |
| TTTCTTGGCT GCGCTGCTTG CCCCATAACC AGACTTCCAC TTGTTGCTTC CAGGACCCAC | 660 |
| GTGATGGTCT CTGGTTGGGT AGGCCTGGGG TTATTCCGAG GACAAAGTAA GGGTGTCATA | 720 |
| GAAGAAAGTC AAGAGAGTAA GCTAGGTMCC CCAAACCTGC ATGGCAGGGA CACAGGACCT | 780 |
| GGACAAGGGC TAGTCCATGT GCCAGGTCCT TTTCGCCTGG GGCAGCCAGG GCAACCTAAA | 840 |
| CCCAGGAAGG GGCAAGTGTA GAAACAGTGA GGGAAAAGTG GGATGAAAGC TACTTGGATC | 900 |
| CAGCACAGAG GGACGAGTGA CCAAAGTGAG CGCCCCAGCG TGGCGCAAGA CTTGGGATCT | 960 |
| GCAGAGAAGC TGTGTAGCTA GGAGCTTTCA ACGGAGCGTG TTAATGTAAA TGTAAATGAA | 1020 |
| GAAATTACCT AATTTTTTTA ATAAAAGAAA GAACAGACAG GCAAAAAAAA AAAAAGGAGG | 1080 |
| AGGAGGAGGA GGAGGATGGT GCGCGCCAAG GGATGCTCTC TATACCTTCG TCAAAGTACC | 1140 |
| TTCTCTTGGG GGACTTCGGA GACTCTGTCA CTGCACCCGA GCACCTTGTC AGCCTCAGAG | 1200 |
| ACTCGGGGCC TCGTGGGCAC TCCAAGAGTT TGGGACGGGG CTTCCTCCCG CCTCCAAAGT | 1260 |
| GATACGAAGG TAGTTGCAGG GAATGTGTGT CTCTCCTCAG CGCACAAGCC CAGGAGGAGG | 1320 |
| TCCCCACGCG TCATGAACTT GGAGACGGGC AGCCGGGGCT CAGAGTTCGG CATGAGCGCA | 1380 |
| GTGAGCTGCG GCAATGGGAA ACTCCGACAG TGGTTGATCG ACCAGATCGA CAGCGGCAAG | 1440 |
| TACCCCGGGC TGGTGTGGGA GAACGAGGAG AAGAGCGTCT TCCGCATCCC GTGGAAACAC | 1500 |
| GCGGGCAAGC AGGACTACAA TCGTGAGGAG GACGCTGCCC TCTTCAAGGT TAGCAGCATT | 1560 |
| CAGGGATCCC TGGCAGGGG TGGGGTGGG GATGGGGAAT CTGAAAGCTC TGAATGTCTG | 1620 |
| TGGCTCCCGG GCAAGGGACT AAGAGGTGGG CTCCTGCAAG GAGGAGGCCA GAGCATCAAG | 1680 |
| CATTGGACCC TGCTTAGGCA AAGTCCCCAG GAGAAGGGAA AGAGGTTGCA AACTCTCCGG | 1740 |
| GGATTGCATA CACAAGAAAC CAGGTCCCAA TACTGTTTGT GTGGAGGAAA GAACTTCCAG | 1800 |
| CTTCAGGGGC ATCTCTGGGG GACCGAGGTT CCGTTTGCAT AGCCCATTCG CTGTTTCCTG | 1860 |

-continued

```
CCACCACCAC CGACTGCTAG GGCCACTCTC TGCTTCCCTG TCTCTCTGTG TTTTGTTATT    1920

TTTCTGAGTT TCTCTCTCTG GGTTTTGTTT CTTTGATTGG GCACCTCTAC TGTCTGGTTC    1980

TAGTTCTAGA AGCTGCGATC TCTGATTTTC TTTCTTTGAG TAGCTTTGAC TATTCCGAGT    2040

CTTTCTCTGG TATCCCCCTC CGACCCCGTG TGAGTCCCTT AGGACTGATG TCCCCAGAGA    2100

ACTGGCTCAC TGAACTGTGA AGCCCCCAGC CTCCACCTGC CAGCAGGCCG AGGAAGGGGA    2160

CTTCCTGCGG GAATTTGTTC AAAGTACCTC TGTGATTTTG TAGATGTCCT CTCTGGGGCC    2220

TGCCCCCTCC ACAGCTCTGT CCCCAGTCTT GCCCACACTT GATTCAGGCG CTGGGCGTGT    2280

ACAGCCCATA CTAGGGGTCT CAGGACCCCA CTAACATCAT GTTCCACATT TCAGGCAACA    2340

GCAAATTTGA AACAGTAACC TTCCTTGCTG AAATGCAATC CATAGAATTC TTTTGACGCT    2400

CTGGGCTTGA CTTTTCTTAT CATCGTTCTT AGGCTTGGGC ATTGTTTAAA GGCAAGTTCC    2460

GAGAAGGGAT CGACAAGCCA GATCCTCCTA CTTGGAAGAC AAGATTACGA TGTGCTCTGA    2520

ACAAGAGCAA TGACTTTGAG GAATTGGTCG AGAGGAGCCA GCTGGATATC TCTGACCCAT    2580

ACAAGGTGTA CAGGATTGTT CCAGAGGGAG CCAAAAAAGG TAAGGGGTTT TCCCAGCCCA    2640

GGTGGCAGGA TAAAGGCATT ATGGCACTCA GAGAGCCCTT CTTCCTAGAG ACAGTCACGT    2700

CCTACCTCTG CTGTAGGTTA AGCCCAGATG TCCTTTTGCC CATGTCCTCT CTGTTATAAG    2760

TGACAACCCT GTGGTGTTAG TATAGGATGA CCTGGCAGAC TTTAAGCCCC ATGGGTGTGT    2820

GGGTTATGCA CTTGAAGGCA TTATTTTCAG TTACTCCATT CAGTTAGGAT CTGGATCAAA    2880

TTTCCAAACA AAATCTGGAA AATCCATTAA ATGTTTACTT ACCTAATATC CTCTAGTAAG    2940

CATTTTCAAG AGGAGAAAGC ACATCCCACA CCCCATACAT ATTCACACTT CTTGTAATAA    3000

AACTGCTAGA GTTTCTGGTT TAACATGGCC TGCTAGGGTG GTTATGAATA TTCAGATCTT    3060

GAGTTCCCTC TCTTCCAACT AGTCTACCTC AAGCAGTGCT CAGGAATCTG CATTTGGTTC    3120

CAACCATACA GGATGCCTTA ACTAGGTACC ATCTCACAAC CAGAAACCAC TTGGTGGATC    3180

ACAGGGATCC TGGGTGGTGT TTCCTTCCCT GGCTGTCACT CACAAGTCAG CAAATGTTTA    3240

ATCAGTTTAA TGGCAAAGAC AAATATCTCT CTAAGAAATT GCTTGAAAAA CAAACAAACA    3300

AACAAAACAA AACAAACCTA AAATACCCGA TTGGTTAATA GGGCTATGCA TTCTAAGAAT    3360

TAAGTGCATA GGTACTTTTA TAAGATTTAA GTCAGTTCCT TGTCTTACTC TGTGTTCTCT    3420

CTTCCTTTTC CCCAAACACA CAGGAGCAAA GCAGCTCACT TTGGATGACA CACAGATGGC    3480

CATGGGCCAC CCCTACCCCA TGACAGCACC TTATGGCTCT CTGCCAGCCC AGGTATGTGG    3540

TAGACTCTTG GTCTTGTGGA AGGCTGGCCC ATGCCCTTTT GACTGGCTCC ACACAGAGAG    3600

GCAAACACAA ATGAAAAGTG TAGGGCTGAC TTCTTATTTG CTATGGCTAG TACACACGCT    3660

GAACAAAAAC TTGGTCAGAG AAGGATGTTT CAGTTCCAGT GTGGTGTCAC TGTCCCTGAC    3720

GCCACAGTTT TGTTGGGGAG TTTGATGTGT CCCACCTGTG GAGAGAGGCT TCCACTGATG    3780

GTCAGATCTT CTGGGAATCA GACCTTTTGT GGAAGTCAAA GGTTTTGGAA GTAGTACTTT    3840

ATCATGTGAA ACCGCAGAGC AGCTGACTTC TCTAGGCGTC CCTGATGTGA ATTACAGTAC    3900

TGTTTTATTC ACTTTGGTGG CTTAAAAAGG GCAGATTTCA CTGCGGTATT CTTGGTGCCG    3960

TGTTCAGCCA TATGATGAAG CCTTACAAAA ATCACAGCTT TATACAATGT CCTCATTGTG    4020

CTTTCAGACC CTCTATGGCT GTTTTTTACC TAGTGTGATA GACAGTCCAT GTCACTTTTT    4080

GGGCAAAATG ACTTGGCTGC TGGACAAAAA AAGGGGTTCC CTGAGGAGTT TGGGTGATAT    4140

GAAAGGACTC CGACACCCMC TGATGTCTTC CTCTTAGCAA TCCCTGTTCT CTGTCAGCAG    4200
```

```
-continued

GTTCATAACT ACATGATGCC ACCCCATGAC AGGAGCTGGA GGGATTATGC CCCTGACCAG    4260

TCACACCCAG AAATCCCATA TCAATGTCCT GTGACGTTTG GCCCACGAGG CCACCACTGG    4320

CAAGGCCCAT CTTGTGAAAA TGGTAAGGAT TGTGCCAGGG CAGCAGACAG AAGAACAACC    4380

TGAGCTCGGG GTGTGGACAG CACCACAGGG CTTTTCCCTA CCATTGAGAT ACCAGAGACA    4440

CATCATATGA AGCTGCTACT GTTGTTGTTG TTGTTGTTGC TGCTGCTGCT GCTGGGGTGG    4500

TGGGGTGGTG GGKTGGTGGG GTGGTGGAGT GGTGGTGGTG GTGGTGGTTG TGGGGTGTTG    4560

GGGTATGTTG CCTTGTCCTG TGAAATGTTG AAGTCCTTAG ATCCATGATA GGCCTCAGTC    4620

TGTGTGGGGA CTTAACTAGA AGACCCCAGA GATCATTCCA AGTAGCTGAA AAGTGCCCCA    4680

TTTTTAATAC ATAGAGAAAA ACATGGATGA CAACAAATTC TCAATGACAA GTAATGTCAA    4740

TTATAAAACT CGTCTATATT TTGTTTTAAC TTGAGTTATC CCTTATTTCC GATGGTGATT    4800

AAGTTGGGGG GTTTGTTGTA TCCCACCTAT CTCCCTAGTC TGTATCTTTC TACTCTCCTG    4860

TAAAGTAGAG AGTTGTACCC AGTCCACCTC AGCAGGAAAT CATTGCTAGT TCATGTCTCT    4920

TGAATAATAA TGAGTCATCT ATAGCTGTTC TTGGTACTAA GGAAGGAAGG ATCAGAGCGA    4980

AAGTAATCCA CAAAGTGTCT CTACAAATGA GTGCCCTGCC CGAAAAGACC CACAGGGGTC    5040

CCCCCATGCT AGCTGGGCTC TCACAGAAGA ACGCCCACT AACCAGACAC AAAAAAATTT     5100

CACAAACTAT GTTCAGTGAG ACTTGGGTCC TTTAGTGTTT ATTTAGGTGA GTGCACCAAG    5160

CTCCACCTCG GGTCCTTTTT TGGCTGTGTA TTTTAAGGTA GAGTCTTGCT AAATTACCAA    5220

GGCTAGGATC TTCCTGCCTT CAACTCTTGA GTAGCTGGGA CTACAATCTT GTTCTARCGG    5280

GCTGAACATA AAACAAGTTT TTAGGACTTR CAAGTTCACT GTTTAAATAT AAGTCTTGAC    5340

ATGGGTCGCC GTGCGAGTAG TTCTTTTATA TTGTTCTGGC AATACTTTAC CTTGTGACAA    5400

TTTCATCAAC ACCCTCACTC AGTCTGTGCA TGCTTACACT AATCTTGCTT TAGTGTGACA    5460

TAACTTCTCT GCTGCCAGAG AACACGGTTC AGCCCCTCCC CCTAGCTAAC AAACAGTGAG    5520

CAGAATAAAT GAGGGTTGAA TAATTAATTC ATCTTTGAAC TAGTCTTATA GAAGTTTGAA    5580

CTCTGACCCT GCTGGTAACT TGCTATGTGG GCTGGTGCAA GTCCCTCTCC TTCTGGGCCT    5640

CAGTTTCCCT ATAGATTTGG AGTGAGCCCC AGGTTTCCAT CCAGAGCTGT ACTGTGGCTC    5700

CTTCCTTCAT CACCCTAATT TTTATCACTG GATGTGGACT TTGGACTTTG TCCCATAATC    5760

ACACGTTATT CTGCTAGCAG GTGCTTAGAG GCTGTCAGGC TTGGGTTGGA GGCCATGGCC    5820

TCTCCCAACT CAAGAGCCTC CCCGCACTCA GACTCGATAC TTAGACATCA TCTGATTTTT    5880

ATTTKCAAAT GCAGGTTGCC AGGTGACAGG AACCTTTTAT GCTTGTGCCC CACCTGAGTC    5940

CCAGGCTCCT GGAATCCCCA TTGAGCCAAG CATAAGGTCT GCTGAAGCCT TAGCGCTCTC    6000

AGGTGAGTGT GGCGCTTCCT GTAAAGCTCC GAGGGAGGGG GCATCTCTCC TCTACTGAGG    6060

TTGGGTGAGG ATTTAGACTC TCGCCTTGCA GGCCCCGGGG TCTGGAGTAG GCATGGTCCA    6120

GGCTATGTGG ACATCACGCT GAGTCAAATA CACTATTAGA AATCTCCACA GCAGTACCAG    6180

CTAGCCAAAT ACTATTTGGA CGATGTCTTT AACCTTCTAC ATCATTACCT GCCCAGTTTT    6240

CCAGGAATGT GTAACCAGGC TCCTCCTCCA GCCGACATTC TCCATTCTCG CAGTGTGGAA    6300

AGGCTTTATA GGCACAAAAG AATGCTGTTT GTCCTTTTAG GGTGTAGGGT TGGCCACAAA    6360

CAGGTGGTCT GAGTTGCTTC CAAGGAACAC TGGTTCTGAA CCCTGGTCTC TGAGAAGTTC    6420

TTATSCCCCC TAAAGGATCA TATAGGTCTG ACTCCCTCAC AACTTTGACA GAATTGCTGA    6480

GCATGTGTGG ATGTGATCTG ATTTTAAAGT TCTGTTACTA AGGAAGCCTG CACTTGGAGA    6540

TACTGACCAG CATTTTAAAA GCCCACACTC CGTGGAAGCA GACATCTTAT GTCCATTTAG    6600
```

```
TCTTTAGATG ATTTTTTTGG ATGTTTTCAA ATGGAATTAT TAGAATTCTC ATCATGCCCT   6660

CGGCTACCTT AAAAGCCTCT GACTGAAAAC ATCAACTGCA TTTTGACAAT TTTAGACACT   6720

TCCCTTGTTC TCGAGGGAGG AAGAAGTTTT AAAATCTAGT TCCTTCCAGC TCTGATGCTC   6780

AGGGAGACTT TGTGAGCCAC TCAAGAACAG CCGAGGAGCA CATCTGGGCA TCAGGGGTTG   6840

TCACAGACAC TAGAATGCTC TAGATCCTCT TCTGGAGCGC CAAAGACTTG TGTGGGTGCC   6900

CCAAGAGTAG GAAATAAACA GCTATTTATA TCTCTGCAAT CTTGTGATTT TGGTGACATT   6960

AAATGAAATG AAACCTGCCC TACCACTCAC CTCAGATGGC CAACGCCCCC TCTCTTTGGG   7020

TGCACCACTT GTGCTGTTCA TAGCTGCAGC TATCGAAGAC ACCATGATGT GGGCTGTCAG   7080

AACTTGCCAT TGAAGAATAC GAGGCTTTTG TGGGTTTCTT CTTCTAGTTT GCATAATTAA   7140

TTATCAACCC TGAGTGCACT TTTCAGAAAG CTATTCTTTC CAGGCATTGT TGGGGCTCCA   7200

ACCACCAGCA CGGGTATCTA TCTCTGCCTG GGGAGCCCTT TGCACACCCA GCTTGCCCTT   7260

TCGGCCCGTG GGTGGTATTT TAAAGTGGCT TCTGAAATCA ACAAAATCAT GTGTCAATAA   7320

ATTCCTGTCT TAAAGCTGTA GAAAACCTAG TTGTTGGGTT CTTTTCAGAG TTGAACACGA   7380

AGCTTAGAGG GATTTCAGGG GGTTTTACAT TAMCCACTGG CTTTTAGAGC AGCTCTCATC   7440

AATTTCTTCC CCTACTCCAA GAGAGCTGAC TTAAAAATAA GAAAATAAAG GTATCATTTT   7500

CCAGAGCCCA GAAATTGTTA TTTTAGTGCC TGTCTCTAAC ATATCTATGT GGGTTTTGTT   7560

GTTGTGTGGT TTTACTTAAT GACATCATGG TAACACCTTA GGGAAGTTCC AGAGCTGAGG   7620

ACACTATTTG CTTTTCTTCT AAGATGTTTC TGTATTTCTT TTACTAATAG AAATCTGTCC   7680

CAGAGGTCAA CTCCAAAATC AAAATTGAGT TGCTGGAAAA CGAATTCCAA TTCGGTAGTA   7740

TTATTTCATA TTGTAGACAA AATGCCACCA CTGTTAACAC CATCATCCGA AAAGCCCTCA   7800

TAACAGGGGT GTGCTTTCTA ATAAAATTTG GCTGAAAATT CAAGAAATAT ATACCTCTCC   7860

CCAAGAGAAG TAAATGGCCA CAACAACATT TGAAAATGAT CGTGTTAGAG AGATCAGTTT   7920

CTTTCCACAA GCTTCTCTTA GTATTCTGTG CTTGAGGTCT AAGAATCTAC AGGGAATAAG   7980

AGCAGCTAAC ATCTCCAAGA CTTCCTTGGT CCTAGGATCT TTCACTTGTT CGTGGAGCAT   8040

CTTGACACTC AAGTGTTCCA CCTGCTGTCC TTCGTATCAG TCTAGTCACC GAGTTTTTGG   8100

GGCTCTGAGC AAGGTGGCAC CTTTTTCAAA TCCATCAGCA CTGACTCCAG AGTTTTGTTC   8160

ACAGACTGCC GGCTGCATAT CTGCCTGTAT TACCGGGACA TCCTCGTGAA AGAGCTGACC   8220

ACGACGAGCC CTGAAGGCTG CCGGATCTCC CACGGACACA CCTATGATGT TAGCAACCTG   8280

GACCAGGTCC TGTTTCCCTA CCCGGACGAC AATGGACAGA GGAAGAACAT TGAGAAGTTG   8340

CTGAGCCACC TGGAGAGGGG ACTGGTCCTC TGGATGGCTC CAGATGGGCT TTATGCCAAA   8400

AGACTCTGCC AGAGTAGGAT CTACTGGGAT GGGCCCCTGG CACTGTGCAG CGATCGGCCC   8460

AACAAGCTAG AAAGAGACCA GACTTGCAAG CTCTTTGACA CACAGCAGTT TCTATCAGGT   8520

AACACACCTC ACAGTCTGTT AGAATGGAGG TGGTGGTGGG TGCTGGCTAT AAAGGTCTCA   8580

AATGGCAGTG TCTGCCTACC CCAGACAGAG GTCTTCCTCC TGAGATCTGT GAGCTCATGC   8640

AGAAATAGAA TTCCTGCCTG ATTCATGCCT AGCCTTTGTC TGTTGTGTAC TCCCCTGATT   8700

AGCAGAGGGC CAGAAAGAGG ATCCATATTT GCTGCCCAGG ATAGACACTG GTGTGGGTTG   8760

ATCTCTTAAT TTATCATCAT TCTTTTCACT CTAGGCTTTT GTTTTGTTTG TTTTGTCAGA   8820

ATATATGTAG CTCAGGCTGG CCTAGAACTC CTGCCTCGGG ATTTTATCTG TACACCAGCA   8880

CATCTGGCCA ATGAATTAAA ATGTGGGCTT TCAGCGGCAT GTGCCCCACC CCCAGAGAGG   8940
```

```
TTTCACTGTG TTGGCTCTCT GCTCTCAGCA AGTTTATCTG CTGACACCTC AGCTCTTTAG    9000

GGGTTTCTAG AAGCAGTTCG GTTGCAGAGA GCAGTGGAAA TCTTTGATGT CTACCCATTC    9060

TGGATTTGCA CCCCACTAGG GACAGTCCCC ATAGGCACAG TTGAGAATTC ATATCTGATC    9120

AGGGCAGAGT CTTCATGCCT GCTCTGTGGA GGCAGCTTTT TAATGTCAGT TCTTTGATGC    9180

AGACAAGACC TGGGAACCTA GCTCTGGGAG GAGGAATAAA GGTTAATGCC AGTGAGTGGA    9240

TGTGGCTTTC TGCTTGTGCT GGGGGAGGAA GCCAAGGCCT TGCACATACA AGGCAAGTGC    9300

TCTGCTCCAA GTGGCGATGC CCCCAGCCAT GGGCAGGTTT CTTTTCAGCA ATCTTGTCTG    9360

TTTCATGTCT CTCAGGCAGG ACTAGCCTCA GCATGACATC CTTGTCAGAG GGGCTTCATT    9420

GGTCCCCTTC TCCCTGTATC ATCCTGTCCC AAAGTGAGA TTGAAGCCTA CTCTGGTTCT     9480

CCAGTTATGG AGTTTTAGAC CTAGTGCCAA GTAGGACACA GCTGCCAACA GCTGGTGAGA    9540

GAAACAGATG CTCTTGGTGC CCAGACACCA CGTGGCCTCC ATGGTTAGCT AGTGAGGTTA    9600

AAAAAATAAC CCTGGGCCAT CAGAACATTG TGACTCTTTA CATTAAAATG TCTCCTTGGC    9660

CTGTGCTGAT TGCTTGACTC AGCATGGCTA CTTTTCTTTT TCTTCTTTGT CTTCTTCTCT    9720

TTGACCTTGT GCATTTCTGT GAGTGTAGTG CTGCAGACCC AAGTTCTTAA GGTTGGGTCA    9780

TGTTCCTTAA GAGTAATGAA GTAAAACCAG TKCCAAGTCA GGAGATCATA TGTGAACTTG    9840

ACCATGTGAT TTTGTGTCTA GGGTCTGCTC TAAGGGCTGG ACTTAGGGGA ACAGAGCCCG    9900

GGCTCTCCCA AAGCAGACTT CCACGTGACT CTGGCTTTCC GTTCACCCGC TTACCAGGT    9960

GTCTGAACAG TTTGGTTTTT TTTTTTCTTT CTTTCTTGTG GGTTTTCAGA GCTGCAAGTG   10020

TTTGCTCACC ATGGCCGGCC AGCACCGAGA TTCCAGGTGA CTCTGTGCTT TGGTGAGGAG   10080

TTTCCAGACC CTCAGAGACA GAGGAAGCTC ATCACAGCTC ATGTGAGTAC CTGGTTACAT   10140

CACCCGTAAA TCACACACTG TGGAGCTGTC CCTTTTAGAG AAGTGGCAAG TGACGAGTAA   10200

ATGTCAGCTC ACCTGGGAAA ATAGATGTAG ACCTTAAAAT AGTGCAGGAG GAAGCAGGCT   10260

CCAGTGAACA CCACAGCTCA GGGAGGCACC CGCAACCTAC TTCCAGACAA ATTCTGTCAC   10320

CACCGAATCA GCAGGGCAGA TGACTTGGAC CCAAGGMTCT GTTTGTTCTG TATTCTTTAT   10380

TGTTTCATAC AGACAGTTAC CTGCCCTTTT ATAGGAATTT TCAATAGTTG GGACCAAGTA   10440

CTGCCCTTCG ACATCTCTGT TTCTTGTGTG GTTTTAAAGA TGCTGTCCTT TCGAGTAGAG   10500

TAGCACTTTC TCCCTGGGAG GCTGCCTGTT ATGTATTATG CTTCATCGGG CCTCCTAACT   10560

TCARATAGTT CCCAGACCCT CGCTTTGTTG CTGGACTTTA GGGAGTTATT TAACAGTTGG   10620

ACAAGGGAGG TGGAGGAGGC TGAGTCTTCC CAGGAATCAG GTAGGTCGGT CTATCCTCAC   10680

AGCTAGGGTT TATTCGGATA ATGTTCATCA CTCACTTAAT AATTAAAAGG TAATTCTGAA   10740

TACATGATGT TTTTTAATTA GAAAATTTTA CTTAATTACA TATCTTGAAA AGTATGCAGT   10800

GTGGAGTAAA GGTTGTGTCC CAGATAGCCA CAATATCTCA GTGCAAATGG GATATTAGCT   10860

CTGATGATAT CTCTTAGTGG AGACTGAAGA CTAGGCATAC AGCGCAATGG AAGGCATTTG   10920

CTAGGCAGTG GTAAAGCCCT GGGTTCTAAA CCCCGCCTAG GATGGGGGTT GGGCACTGAT   10980

GTTGAACATC CAGCCTCCCT TCTCGGTTGG AAAAAGTAAA ATCTAAGAAG CAACAAACGG   11040

GCTGGAGAGA TGGCTCAGTT GTTAAGAGCA CAGGCTGTTC TTCCAGAGGT CCTGAGTTTA   11100

ATTCCTAGAA ACCACATGTG CCTTACAACC ATCTGCAGTG AGCTCTAATG CCATCTTCTG   11160

GTGTGTTTGA AGACTGCTAC AGTGAACTCA CATACATATA AATCTTAAAA AAATAAAAGG   11220

CAATGAAACT ATGATCCTGG CCTTGAGCCT TTTCTCAGTT CTAACTGGTG GTTGATATCA   11280

AATGAGACTG CAGATGTGTG GATGAATCTA GCATAGATAA GCAGTATTTT TTTTTTAAGG   11340
```

```
TAGTGAGTAA ATTCTAGCAT AGATCTCATT TTAAGGACTT TGGGTGCAGT GGGGCTCCGC    11400

AAAAAGGGAG CAACAATAGT CATATAGGCA AAGGGCCTCA AAATGCTGCC CCGTGGTCCA    11460

CAGATGGAAA ACATACATGG TCACCCATGA ACTCTGCTGG TCTCCTTATT ACAGACTTAA    11520

TTCATATGGG TGCTTACAGA GGAATCCTAC CAGACATCAC ATATCAAATA ACAAAGAGGC    11580

TTGATTTATT GATGATTGGT TGTTACAGAG CACACAGCCT GACTTGGTGA GGCTGGCTTT    11640

GACTGGGGAT GCAATCGATG CTTATAAACA AACTAGGTCC ATCAGAGCCA GCGAGCTGCT    11700

GTCTTGTGGC TGRCCAGCTC TGTCTTCTAC TTGTGGTTCA GAGTTCTGTC TATTTCACAG    11760

TCATCTGGTT CTTCAGGATG AGCCCTTCTG TCAGACTCAT GAGCCTCACT TACCCAGCAT    11820

GTTACTTAGC CTTTTAATTT GGTCATCTCA TTCAATAATG TCCAGTTAAC TCATTCGCTA    11880

AATATCAAAT CCAAGAGGCG ATTGGTTTCA AAATGCCATA TTTATCTTCT ATTATAGAAT    11940

CAAGAGTTCT TTTTCCAGGG TTTTTAATTC CAGGTATTGT AAGAGCAAAT GAAACTGGTT    12000

TTTCAAATGG CTCTGAATGT GAACTGCTTC ACTGTGTTAT GTTATCCTGT GCAGCTTGTA    12060

GGTTTTTACT TAGAGTCCTA GGGTCATTTC ATGATGTCCC AATTGTATGG TGTTGAGAAG    12120

AATATTCTAG TGATGTCTTT TTTTCTTAAA TGTCTTATTA AAGGTGGAAC CTCTGCTAGC    12180

CAGACAACTG TATTACTTTG CTCAACAAAA CACTGGACAT TTCCTGAGGG CTACGAGTT    12240

ACCTGAACAC GTTACCACTC CAGATTACCA CCGCTCCCTC CGTCATTCTT CCATCCAAGA    12300

GTGAGAAGAA ATACTCTGAC AGGGCAGCCG GTTGCTGCCC TTTCTCTTTG GAAGAGCTAA    12360

GAAGTGAGTG GGTTTCCACT TGAAGACAAC AACAGGGCTT TGTGAGGAAA ACAGCTGTAT    12420

CTGCTCAACA GAGGAGCTTC CCCCAGAAGA GTGCCTGTCA GTCATCCAGG TCTTGACAAG    12480

TGCCAGGACT TGGGTGACTG TGCCCTGGCT TATAACTGTG AAACTTGATC CGAATTC      12537

(2) INFORMATION FOR SEQ ID NO:5:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

ATCCTGGAAC ACGC                                                           14

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GCACACGAAC TGCCTTCCA                                                      19

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO:7:

CAGCCCGGGG TACTTGCCGC TGTC                                              24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

AGACCTTATG CTTGGCTCAA TGGG                                              24

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Gly Tyr Glu Leu Pro His Glu Val Thr Thr Pro Asp Tyr His Arg
1               5                   10                  15

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

TGCAGAAGTG AAACTGAGG                                                    19

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

TGCAGAAGTG AAACTGAG                                                     18

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

TGCAGAAGTG AAACCTGG                                                        18

(2) INFORMATION FOR SEQ ID NO:13:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:13:

TGCAGAAGTG AACATGAG                                                        18

(2) INFORMATION FOR SEQ ID NO:14:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:14:

TGCAGAAGTG GTCCTGAG                                                        18

(2) INFORMATION FOR SEQ ID NO:15:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:15:

GCTAGAAGTG AAACTGAG                                                        18

(2) INFORMATION FOR SEQ ID NO:16:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:16:

AAAGGAAGTG AAACCAAG                                                        18

(2) INFORMATION FOR SEQ ID NO:17:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:17:

TGAGGAACTG AAAACAGA                                                        18

(2) INFORMATION FOR SEQ ID NO:18:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:18:

GGGAAAGTGA AACTAG              16

(2) INFORMATION FOR SEQ ID NO:19:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:19:

CTGGACATCT CAGACCCGTA CAAAGTG         27

(2) INFORMATION FOR SEQ ID NO:20:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:20:

CTTGACATTT TTCATTCTTG AATAGAG         27

(2) INFORMATION FOR SEQ ID NO:21:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:21:

TGCCCTCAGC TCCGAGTCCA G           21

(2) INFORMATION FOR SEQ ID NO:22:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:22:

AACCATTTTC ACAAGCTG            18

(2) INFORMATION FOR SEQ ID NO:23:

(i) SEQUENCE CHARACTERISTICS:

(A) LENGTH: 38 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:23:

GGATCCGGAT CCATGAACTG GAGGGCGGCG GCCGAGGC                                    38

(2) INFORMATION FOR SEQ ID NO:24:

(i) SEQUENCE CHARACTERISTICS:
          (A) LENGTH: 1353 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:24:

ATGAACCTGG AGGGCGGCGG CCGAGGCGGA GAGTTCGGCA TGAGCGCGGT GAGCTGCGGC            60

AACGGGAAGC TCCGCCAGTG GCTGATCGAC CAGATCGACA GCGGCAAGTA CCCCGGGCTG          120

GTGTGGGAGA ACGAGGAGAA GAGCATCTTC CGCATCCCCT GGAAGCACGC GGGCAAGCAG          180

GACTACAACC GCGAGGAGGA CGCCGCGCTC TTCAAGGCTT GGGCACTGTT TAAAGGAAAG          240

TTCCGAGAAG GCATCGACAA GCCGGACCCT CCCACCTGGA AGACGCGCCT GCGGTGCGCT          300

TTGAACAAGA GCAATGACTT TGAGGAACTG GTTGAGCGGA GCCAGCTGGA CATCTCAGAC          360

CCGTACAAAG TGTACAGGAT TGTTCCTGAG GGAGCCAAAA AAGGAGCCAA GCAGCTCACC          420

CTGGAGGACC CGCAGATGTC CATGAGCCAC CCCTACACCA TGACAACGCC TTACCCTTCG          480

CTCCCAGCCC AGGTTCACAA CTACATGATG CCACCCCTCG ACCGAAGCTG GAGGGACTAC          540

GTCCCGGATC AGCCACACCC GGAAATCCCG TACCAATGTC CCATGACGTT TGGACCCCGC          600

GGCCACCACT GGCAAGGCCC AGCTTGTGAA AATGGTTGCC AGGTGACAGG AACCTTTTAT          660

GCTTGTGCCC CACCTGAGTC CCAGGCTCCC GGAGTCCCCA CAGAGCCAAG CATAAGGTCT          720

GCCGAAGCCT TGGCGTTCTC AGACTGCCGG CTGCACATCT GCCTGTACTA CCGGGAAATC          780

CTCGTGAAGG AGCTGACCAC GTCCAGCCCC GAGGGCTGCC GGATCTCCCA TGGACATACG          840

TATGACGCCA GCAACCTGGA CCAGGTCCTG TTCCCCTACC AGAGGACAAG TGGCCAGAGG          900

AAAAACATTG AGAAGCTGCT GAGCCACCTG GAGAGGGGCG TGGTCCTCTG GATGGCCCCC          960

GACGGGCTCT ATGCGAAAAG ACTGTGCCAG AGCAGGATCT ACTGGGACGG GCCCCTGGCG         1020

CTGTGCAACG ACCGGCCCAA CAAACTGGAG AGAGACCAGA CCTGCAAGCT CTTTGACACA         1080

CAGCAGTTCT TGTCAGAGCT GCAAGCGTTT GCTCACCACG GCCGCTCCCT GCCAAGATTC         1140

CAGGTGACTC TATGCTTTGG AGAGGAGTTT CCAGACCCTC AGAGGCAAAG AAAGCTCATC         1200

ACAGCTCACG TAGAACCTCT GCTAGCCAGA CAACTATATT ATTTTGCTCA ACAAAACAGT         1260

GGACATTTCC TGAGGGGCTA CGATTTACCA GAACACATCA GCAATCCAGA AGATTACCAC         1320

AGATCTATCC GCCATTCCTC TATTCAAGAA TGA                                     1353

(2) INFORMATION FOR SEQ ID NO:25:

(i) SEQUENCE CHARACTERISTICS:
          (A) LENGTH: 450 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:25:

```
Met Asn Leu Glu Gly Gly Gly Arg Gly Gly Glu Phe Gly Met Ser Ala
1               5                   10                  15

Val Ser Cys Gly Asn Gly Lys Leu Arg Gln Trp Leu Ile Asp Gln Ile
            20                  25                  30

Asp Ser Gly Lys Tyr Pro Gly Leu Val Trp Glu Asn Glu Glu Lys Ser
            35                  40                  45

Ile Phe Arg Ile Pro Trp Lys His Ala Gly Lys Gln Asp Tyr Asn Arg
    50                  55                  60

Glu Glu Asp Ala Ala Leu Phe Lys Ala Trp Ala Leu Phe Lys Gly Lys
65                  70                  75                  80

Phe Arg Glu Gly Ile Asp Lys Pro Asp Pro Thr Trp Lys Thr Arg
                85                  90                  95

Leu Arg Cys Ala Leu Asn Lys Ser Asn Asp Phe Glu Glu Leu Val Glu
                100                 105                 110

Arg Ser Gln Leu Asp Ile Ser Asp Pro Tyr Lys Val Tyr Arg Ile Val
            115                 120                 125

Pro Glu Gly Ala Lys Lys Gly Ala Lys Gln Leu Thr Leu Glu Asp Pro
130                 135                 140

Gln Met Ser Met Ser His Pro Tyr Thr Met Thr Thr Pro Tyr Pro Ser
145                 150                 155                 160

Leu Pro Ala Gln Val His Asn Tyr Met Met Pro Pro Leu Asp Arg Ser
                165                 170                 175

Trp Arg Asp Tyr Val Pro Asp Gln Pro His Pro Glu Ile Pro Tyr Gln
                180                 185                 190

Cys Pro Met Thr Phe Gly Pro Arg Gly His His Trp Gln Gly Pro Ala
                195                 200                 205

Cys Glu Asn Gly Cys Gln Val Thr Gly Thr Phe Tyr Ala Cys Ala Pro
                210                 215                 220

Pro Glu Ser Gln Ala Pro Gly Val Pro Thr Glu Pro Ser Ile Arg Ser
225                 230                 235                 240

Ala Glu Ala Leu Ala Phe Ser Asp Cys Arg Leu His Ile Cys Leu Tyr
                245                 250                 255

Tyr Arg Glu Ile Leu Val Lys Glu Leu Thr Thr Ser Ser Pro Glu Gly
                260                 265                 270

Cys Arg Ile Ser His Gly His Thr Tyr Asp Ala Ser Asn Leu Asp Gln
            275                 280                 285

Val Leu Phe Pro Tyr Pro Glu Asp Asn Gly Gln Arg Lys Asn Ile Glu
            290                 295                 300

Lys Leu Leu Ser His Leu Glu Arg Gly Val Val Leu Trp Met Ala Pro
305                 310                 315                 320

Asp Gly Leu Tyr Ala Lys Arg Leu Cys Gln Ser Arg Ile Tyr Trp Asp
                325                 330                 335

Gly Pro Leu Ala Leu Cys Asn Asp Arg Pro Asn Lys Leu Glu Arg Asp
            340                 345                 350

Gln Thr Cys Lys Leu Phe Asp Thr Gln Gln Phe Leu Ser Glu Leu Gln
            355                 360                 365

Ala Phe Ala His His Gly Arg Ser Leu Pro Arg Phe Gln Val Thr Leu
    370                 375                 380

Cys Phe Gly Glu Glu Phe Pro Asp Pro Gln Arg Gln Arg Lys Leu Ile
385                 390                 395                 400
```

```
    Thr Ala His Val Glu Pro Leu Leu Ala Arg Gln Leu Tyr Tyr Phe Ala
                    405                 410                 415

Gln Gln Asn Ser Gly His Phe Leu Arg Gly Tyr Asp Leu Pro Glu His
                420                 425                 430

Ile Ser Asn Pro Glu Asp Tyr His Arg Ser Ile Arg His Ser Ser Ile
                435                 440                 445

Gln Glu
        450
```